US009192685B2

(12) United States Patent
Allemann et al.

(10) Patent No.: US 9,192,685 B2
(45) Date of Patent: Nov. 24, 2015

(54) TARGETING CONSTRUCT COMPRISING ANTI-POLYMER ANTIBODY AND CONTRAST/THERAPEUTIC AGENTS BINDING TO THE SAME

(75) Inventors: Eric Allemann, Plan-les-Ouates (CH); Thierry Bettinger, Plan-les-Ouates (FR); Philippe Bussat, Plan-les-Ouates (FR); Mathieu Hauwel, Plan-les-Ouates (FR); Feng Yan, Plan-les-Ouates (CH)

(73) Assignee: Bracco Suisse S.A., Manno (CH)

( * ) Notice: Subject to any disclaimer, the term of this patent is extended or adjusted under 35 U.S.C. 154(b) by 1246 days.

(21) Appl. No.: 13/123,201

(22) PCT Filed: Oct. 7, 2009

(86) PCT No.: PCT/EP2009/063020
§ 371 (c)(1),
(2), (4) Date: Apr. 7, 2011

(87) PCT Pub. No.: WO2010/040772
PCT Pub. Date: Apr. 15, 2010

(65) Prior Publication Data
US 2011/0200530 A1 Aug. 18, 2011

(30) Foreign Application Priority Data
Oct. 7, 2008 (EP) .................................... 08166011

(51) Int. Cl.
| A61K 49/22 | (2006.01) |
| A61K 39/44 | (2006.01) |
| A61K 47/48 | (2006.01) |
| A61K 49/00 | (2006.01) |
| C07K 16/28 | (2006.01) |
| C07K 16/44 | (2006.01) |
| A61K 49/04 | (2006.01) |

(52) U.S. Cl.
CPC ............... *A61K 49/223* (2013.01); *A61K 39/44* (2013.01); *A61K 47/48823* (2013.01); *A61K 47/48869* (2013.01); *A61K 49/0002* (2013.01); *A61K 49/0466* (2013.01); *C07K 16/2851* (2013.01); *C07K 16/2863* (2013.01); *C07K 16/44* (2013.01); *C07K 2317/31* (2013.01)

(58) Field of Classification Search
CPC ............ A61K 39/44; A61K 47/48823; A61K 47/48869; A61K 49/222; A61K 49/223; A61K 49/227; C07K 16/44; C07K 2317/31
USPC ....................... 424/9.5, 9.51, 9.52, 450, 178.1
See application file for complete search history.

(56) References Cited

U.S. PATENT DOCUMENTS

| 4,276,885 A | 7/1981 | Tickner et al. |
| 4,816,567 A | 3/1989 | Cabilly et al. |
| 4,946,778 A | 8/1990 | Ladner et al. |
| 5,271,928 A | 12/1993 | Schneider et al. |
| 5,387,410 A | 2/1995 | Bosworth et al. |
| 5,413,774 A | 5/1995 | Schneider et al. |
| 5,545,395 A | 8/1996 | Tournier et al. |
| 5,585,112 A * | 12/1996 | Unger et al. ................... 424/450 |
| 5,597,549 A | 1/1997 | Schneider et al. |
| 5,605,673 A | 2/1997 | Schutt et al. |
| 5,711,933 A | 1/1998 | Bichon et al. |
| 5,827,504 A | 10/1998 | Yan et al. |
| 5,837,821 A | 11/1998 | Wu |
| 5,853,723 A | 12/1998 | Jacobs et al. |
| 5,969,108 A | 10/1999 | McCafferty et al. |
| 6,197,333 B1 * | 3/2001 | Onyuksel et al. ............. 424/450 |
| 6,217,849 B1 | 4/2001 | Tournier et al. |
| 6,333,021 B1 | 12/2001 | Schneider et al. |
| 2001/0028881 A1 | 10/2001 | Roffler et al. |
| 2003/0026764 A1 | 2/2003 | Griffiths |

FOREIGN PATENT DOCUMENTS

| AU | 9057621 B | 1/1991 |
| EP | 0404097 A2 | 6/1990 |
| EP | 0324938 B1 | 11/1993 |
| WO | 92/10166 A1 | 6/1992 |
| WO | 94/09829 A1 | 5/1994 |
| WO | 96/39124 A1 | 12/1996 |
| WO | 97/29782 A1 | 8/1997 |
| WO | 98/18501 A2 | 5/1998 |
| WO | 99/39738 A1 | 8/1999 |
| WO | 01/09188 A1 | 2/2001 |
| WO | 02/09483 A1 | 1/2002 |
| WO | 02/55544 A2 | 7/2002 |
| WO | 02/094853 A2 | 11/2002 |
| WO | 03/074005 A2 | 9/2003 |
| WO | 03/084574 A1 | 10/2003 |

(Continued)

OTHER PUBLICATIONS

PCT International Preliminary Report on Patentability (Chapter I) for PCT/EP2009/063020, mail date Apr. 21, 2011.
Babcook, J.S. et al., "A novel strategy for generating monoclonal antibodies from single, isolated lymphocytes producing antibodies of defined specificities", Proc. Natl. Acad. Sci. USA, Immunology, vol. 93, pp. 7843-7848, Jul. 1996.
Bird, R.E. et al., "Single-Chain Antigen-Binding Proteins", Science, New Series, vol. 242, No. 4877, pp. 243-426, Oct. 1988.
Briley-Saebo, K.C. et al., "Targeted Molecular Probes for Imaging Atherosclerotic Lesions With Magnetic Resonance Using Antibodies That Recognize Oxidation-Specific Epitopes", Circulation, Journal of the American Heart Association, vol. 117, pp. 3206-3215, 2008, ISSN: 1524-4539.

(Continued)

*Primary Examiner* — Michael G Hartley
*Assistant Examiner* — Leah Schlientz
(74) *Attorney, Agent, or Firm* — VIVICAR Law, PLLC

(57) ABSTRACT

Pharmaceutical kit comprising (i) a targeting construct which comprises a targeting ligand and an anti-polymer antibody and (ii) a polymer-containing liposome or gas-filled microvesicle capable of binding or associating to said construct. Also disclosed are methods of preparing and of administering said assembly, as well as an assembly comprising said targeting construct and said liposome or gas-filled microvesicle.

10 Claims, 2 Drawing Sheets

(56) References Cited

FOREIGN PATENT DOCUMENTS

| WO | 2004/069284 A2 | 8/2004 |
|---|---|---|
| WO | 2005/063305 A1 | 7/2005 |
| WO | 2005/063306 A1 | 7/2005 |
| WO | 2005/117832 A1 | 12/2005 |
| WO | 2006/031885 A2 | 3/2006 |
| WO | 2006/111490 A1 | 10/2006 |
| WO | 2007/109475 A2 | 9/2007 |
| WO | 2008/073458 A2 | 6/2008 |
| WO | 2008/075191 A2 | 6/2008 |

OTHER PUBLICATIONS

Cassidy, P.J. et al., "Molecular imaging perspectives", Journal of the Royal Society Interface, vol. 2, pp. 133-144, 2005.

Cheng, Tian-Lu et al., "Monoclonal Antibody-Based Quantitation of Poly(ethylene glycol)-Drivatized Proteins, Liposomes, and Nanoparticles", Bioconjugate Chemistry, vol. 16, No. 5, pp. 1225-1231, 2005, ISSN: 1043-1802, XP002515101.

Goins, B.A. et al. "The use of scintigraphic imaging as a tool in the development of liposome formulations", Progress in Lipid REsearch, vol. 40, pp. 95-123, 2001, Elsevier Science Ltd.

Golman, K. et al., "Molecular imaging with endogenous substances", PNAS, vol. 100, No. 18, pp. 10435-10439, Sep. 2003.

Han, Z. et al., "Noninvasive assessment of cancer response to therapy", Nature Medicine: Technical Reports, vol. 14, No. 3, pp. 343-349, Mar. 2008.

Hollinger, P. et al., "'Diabodies': small bivalent and bispecific antibody fragments", Proc. Natl. Acad. Sci. USA, vol. 90, No. 14, 1993, pp. 6444-6448.

Hollinger, P. et al, "Engineered Antibody Fragments and the Rise of Single Domains", Nature Biotechnology, vol. 23, No. 9, 2005, pp. 1126-1136.

Johansson, E., et al., "Perfusion Assessment With Bolus Differentiation: A Technique Applicable to Hyperpolarized Tracers", Magnetic Resonance in Medicine, vol. 52, pp. 1043-1051, 2004.

Kelly, K.A. et al., "Detection of Early Prostate Cancer Using a Hepsin-Targeted Imaging Agent", Cancer Research, vol. 68, No. 7, pp. 2286-2291, 2008.

Kohler, G. et al., "Continuous cultures of fused cells secreting antibody of predefined specificity", Nature, vol. 256, pp. 495-497, Aug. 1975.

Lupold, S.E. et al., "Identification and Characterization of Nuclease-stabilized RNA Molecules That Bind Human Prostate Cancer Cells via the Prostate-specific Membrane Antigen", Cancer Research, vol. 62, pp. 4029-4033, 2002.

Malsten, M., in Surfactants and POlymers in Drug Delivery, Chapter 4: Liposomes, pp. 87-113, Marcel Dekker Inc., 2002.

Making and Using Antibodies: A practical handbook, Chapters 4, 5 and 9 CRC press, 2007.

Okamoto, T. et al., "Optimal Construction of Non-immune scFv Phage Display Libraries From Mouse Bone Marrow and Spleen Established to Select Specific scFvs Efficiently Binding to Antigen", Biochemical and Biophysical Research Communications, vol. 323, No. 2, 2004, pp. 583-591.

Pasqualni, R. et al., "Hybridoma-Free Generatino fo Monoclonal Antibodies", Proc Natl Acad Sci USA, vol. 101, No. 1, 2004, pp. 257-259.

Quiocho, F.A., "Making of the minibody", Nature: Protein Engineering, vol. 362, pp. 293-294, Mar. 1993.

Schnyder, Anita et al., "Targeting of skeletal muscle in vitro using biotinylated immunoliposomes", Biochemical Journal, vol. 377, No. 1, pp. 61-67, 2004, The Biochemical Society, London, GB LNKD-DOI:10.1042/BJ2003103, XP002560984.

Sharma, V. et al., "Molecular Imaging of Gene Expression and Protein Function in Vivo With PET and SPECT", Journal of Magnetic Resonance Imaging, vol. 16, pp. 336-351, 2002.

Sweeney, P. et al., "Anti-Vascular Endothelial Growth Factor Receptor 2 Antibody Reduces Tumorigenicity and Metastasis in Orthotopic Prostate Cancer Xenografts via Induction of Endothelial Cell Apoptosis and Reduction of Endothelial Cell Matrix Metalloproteinase Type 9 Production", Clincal Cancer Research, vol. 8, pp. 2714-2724, 2002.

Torchilin, V.P., "Targeted Pharmaceutical Nanocarriers for Cancer Therapy and Imaging", The AAPS Journal, vol. 9, No. 2 pp. E128-E147, 2007.

von Wronski, M.A. et al., "Tuftsin Bindsd Neuropilin-1 through a Sequence Similar to That Encoded by Exon 8 of Vascular Endothelial Growth Factor", The Journal of Biological Chemistry, vol. 281, No. 9, pp. 5702-5710, Mar. 2006, JBC Papers in Press.

Wu, B.P. et al., "Construction and selection of the natural immune Fab antibody phage display library from patients with colorectal cancer", World Journal of Gastroenterology, vol. 7, No. 6, 2001, pp. 811-815.

Yau, K.Y., et al., "Affinity maturation of a V(H)H by mutational hotspot randomization", Journal of Immunological Methods, vol. 297, Nos. 1-2, 2005, pp. 213-224.

PCT International Search Report for PCT/EP2009/063020, mail date May 25, 2010.

PCT Written Opinion of the International Searching Authority for PCT/EP2009/063020, mail date May 25, 2010.

First Office Action for Australian application No. AU2009301141, mail date Aug. 12, 2014.

First Office Action for Chinese application No. 200980142131.0, mail date Mar. 30, 2012 (English translation).

Second Office Action for Chinese application No. 200980142131.0, mail date Feb. 28, 2013 (English translation).

Office Action for Japanese application No. 2011-530477, mail date Oct. 22, 2013 (English translation with agent's Office Action Summary).

\* cited by examiner

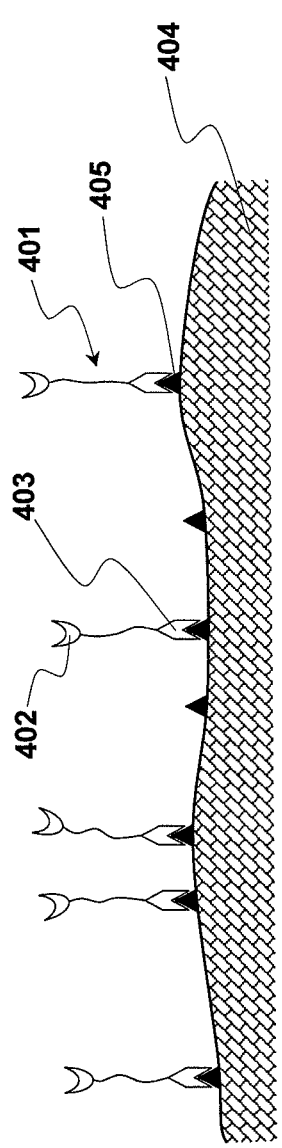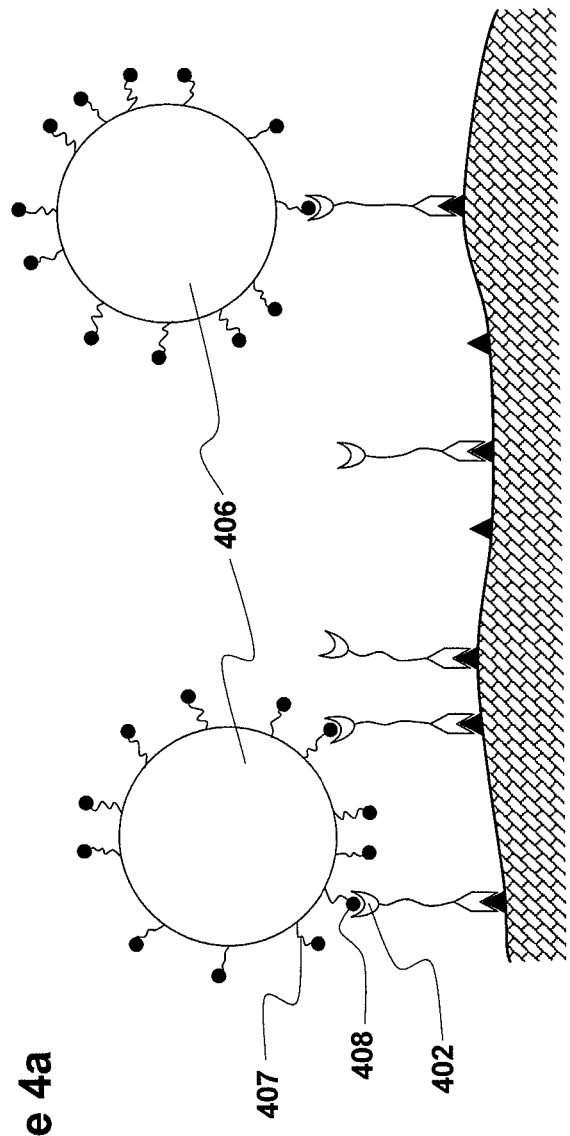
Figure 4a
Figure 4b

TARGETING CONSTRUCT COMPRISING ANTI-POLYMER ANTIBODY AND CONTRAST/THERAPEUTIC AGENTS BINDING TO THE SAME

This application is the national stage application of corresponding international application number PCT/EP2009/063020 filed Oct. 7, 2009, which claims priority to and the benefit of European application no. 08166011.0, filed Oct. 7, 2008, all of which are hereby incorporated by reference.

TECHNICAL FIELD

The present invention relates to an assembly comprising (i) a targeting construct which comprises a targeting ligand and an anti-polymer antibody and (ii) a polymer-containing liposome or gas-filled microvesicle capable of binding or associating to said assembly. The invention further relates to methods of preparing and of administering said assembly, as well as pharmaceutical kits comprising said targeting construct and said liposome or gas-filled microvesicle.

BACKGROUND OF THE INVENTION

Diagnostic imaging employing agents capable of enhancing the images obtainable with different imaging techniques (known as "contrast agents" or "image enhancing agents") has become a widely adopted practice in the diagnostic field.

Rapid development of contrast agents in recent years has generated a number of different formulations, which are useful in contrast-enhanced imaging of organs and tissue of the human or animal body.

A class of contrast agents, particularly useful for ultrasound contrast imaging, includes suspensions of gas bubbles of nano- and/or micro-metric size dispersed in an aqueous medium. Of particular interest are those formulations where the gas bubbles are stabilized, for example by using emulsifiers, oils, thickeners or sugars, or by entrapping or encapsulating the gas or a precursor thereof in a variety of systems. These stabilized gas bubbles are generally referred to in the art with various terminologies, such as, for instance, "microvesicles", "microspheres", "microbubbles", "microcapsules" or "microballoons". In the present description and claims, the term "microvesicles" is used to identify any of the above described stabilized gas-bubbles.

Other contrast agents include iodinated products (such as iopamidol or iomeprol), which are widely employed in X-ray contrast analysis, in particular computer tomography (CT) X-ray, whilst compounds containing paramagnetic ions (such as ProHance® or MultiHance®, Bracco Imaging), are widely employed in MRI analysis. The active (X-ray or MRI) imaging agent can advantageously be incorporated in liposome structures (see e.g. Ref. 1 or Ref. 2).

Gas-filled microvesicles may include in their formulation a polymer, in particular a hydrophilic polymer (e.g. polyethyleneglycol, PEG), which has been found useful, for instance, for reducing immunogenicity, improve biocompatibility, reduce receptor mediated uptake by the reticuloendothelial system (RES) and/or increase the serum half-life of the contrast agent. For similar reasons, polymers, such as PEG, have also been included in the formulation of liposomes employed as carriers for contrast or therapeutic agents.

More recently, gas-filled microvesicles have been modified with suitable target-specific components, capable of selectively binding the microvesicles to a desired organ or tissue.

For instance, microvesicles or liposomes can be associated (e.g. by inclusion in their boundary envelope) with specific components which are capable of binding to a determined target or region within a patient's body (known as "targeting ligands"), so to selectively enhance the imaging of said target or region.

Examples of targeting ligands include, for instance, peptides, proteins or antibodies, capable of binding to a specific organ or tissue such as, for instance, angiogenic inflammatory or thrombosed tissue.

For instance, the structure of a microvesicle or of a liposome can be modified by binding the targeting ligand to suitable molecules which are employed for the formation of the microvesicle's or liposome's envelope. The targeting moiety can be directly linked to the envelope-forming molecule or through a suitable spacer. This methodology thus typically entails a modification of the components forming the microvesicle or liposome envelope, to allow the binding thereof to the desired targeting moiety.

The Applicant has now found a new method where the targeting ligand is associated with a polymer-containing liposome or gas-filled microvesicle by means of an antibody capable of specifically recognising said polymeric component comprised in said liposome or microvesicle.

SUMMARY OF THE INVENTION

An aspect of the invention relates to a pharmaceutical kit comprising:
  a) a first composition comprising a liposome or a gas-filled microvesicle, or a precursor thereof, having a stabilizing envelope comprising a plurality of polymer molecules; and
  b) a second composition comprising a targeting construct, said construct comprising a targeting ligand and an antibody capable of selectively binding to said polymer.

According to a preferred embodiment, said polymer is a hydrophilic polymer. Preferably said polymer contains repeating oxyethylene units, and more preferably it is terminated with a methoxy group. According to a particularly preferred embodiment, said polymer is polyethylene glycol. Preferably, said antibody thus binds to a hydrophilic polymer, more preferably it binds to a polymer containing repeating oxyethylene units, and even more preferably it binds to a polymer containing repeating oxyethylene units and terminated with a methoxy group. According to a particular preferred embodiment, said antibody binds to polyethylene glycol.

According to another preferred embodiment, the molar amount of said polymer is of at least 0.05% with respect to the total amount of components of said stabilizing envelope, preferably of at least 0.2% and even more preferably of at least 1%.

According to a particular preferred embodiment, said polymer is covalently bound to an amphiphilic compound, preferably a phospholipid.

According to a further preferred embodiment, said microvesicles have a stabilizing envelope comprising an amphiphilic material, preferably a phospholipid; preferably said amphiphilic material represents more than 50% by moles of the total components of the stabilizing envelope and more preferably more than 80% and even more preferably more than 90%.

According to a further aspect, the invention relates to a liposome or a gas-filled microvesicle, or a precursor thereof, comprising: a) a plurality of polymer molecules; b) an antibody bound to said polymer; and c) a targeting ligand associated with said antibody.

Preferred antibodies and polymers are as above defined.

A further aspect of the invention relates to a method for administering a liposome or a gas-filled microvesicle to a body part of a patient which comprises the steps of:
 a) administering a first composition comprising a targeting construct, said construct comprising: (i) a targeting ligand capable of selectively binding to a molecule or tissue in said body part and (ii) an antibody capable of selectively binding to a polymer molecule;
 b) administering a second composition comprising said liposome or said gas-filled microvesicle having a stabilizing envelope comprising a plurality of said polymer molecules.

According to a preferred embodiment, said liposome or gas-filled microvesicle is administered after a time sufficient to allow the targeting construct to reach the selected body part.

FIGURES

FIG. 4 illustrates an example of use of the targeting construct of the invention together with a contrast/therapeutic agent.

DETAILED DESCRIPTION OF THE INVENTION

Definitions

Figure 2:
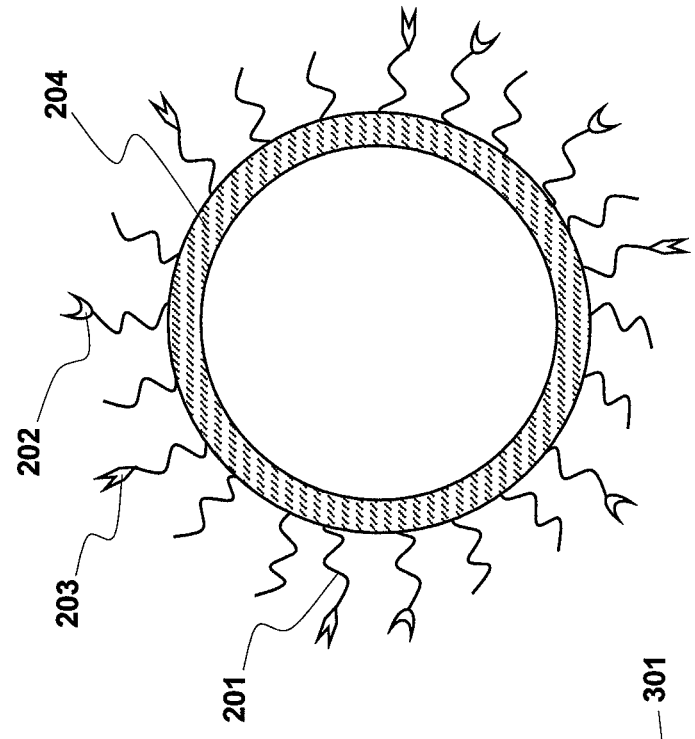
FIGS. 1 to 3 illustrate examples of targeting constructs according to the invention.

The expression "associated with", particularly when referred to the association of a targeting ligand with an antibody capable of selectively binding to a hydrophilic polymer, includes within its meaning any covalent or non-covalent binding capable of creating a relatively stable interaction between the components involved in the association.

The expression "non-covalent binding" includes intermolecular interactions among two or more molecules which do not involve a covalent bond such as, for instance, ionic or electrostatic interactions, dipole-dipole interactions, hydrogen bonding, hydrophilic or hydrophobic interactions, van der Waal's forces and combinations thereof. Non-covalent binding further include interactions between moieties of an affinity binding pair, such as, for instance, the interaction between avidin or streptavidin and biotin; protein A or G binding and Fc-region of immunoglobulin; oligonucleotides and complementary sequences, e.g. Polydesoxyadenylic acid and Polydesoxythimidylic acid, or Polydesoxyguanylic acid and Polydesoxycytidylic acid; Ni-NTA (nitrilotriacetic acid, nickel salt) and Poly histidine-tagged ligand.

The expression "contrast agent" includes within its meaning any compound, construct, composition or formulation which may be used in connection with methods for imaging a region of interest in a patient and/or aiding in the diagnosis of the presence or absence of a disease in a patient, and which is in general capable of enhancing the imaging of a diagnostic imaging technique. Examples of diagnostic techniques, include ultrasound imaging, magnetic resonance imaging, X-ray imaging (in particular computed tomography), optical imaging, nuclear imaging or molecular imaging. Examples of suitable contrast agents include, for instance, gas-filled microvesicles (e.g. for ultrasound imaging), iodinated compounds, iodinated liposomes; magnetite nanoparticles; paramagnetic ion chelated complexes; fluorescent dyes; compounds comprising a hyperpolarized atom or radiopharmaceutical agents.

The term "therapeutic agent" includes within its meaning any substance, composition, formulation, or drug delivery system which may be used in any therapeutic application, such as in methods for the treatment of a disease in a patient, as well as any substance which is capable of exerting or responsible to exert a biological or physiological effect in vitro and/or in vivo. Therapeutic agents thus include any compound or material capable of being used in the treatment (including prevention, alleviation, pain relief or cure) of any pathological status in a patient (including malady, affliction, disease lesion or injury), such as drugs, pharmaceuticals, bioactive agents, cytotoxic agents, chemotherapy agents, radiotherapeutic agents, proteins, natural or synthetic peptides, including oligopeptides and polypeptides, vitamins, steroids and genetic material, including nucleosides, nucleotides, oligonucleotides, polynucleotides and plasmids. Among these, drugs or pharmaceuticals are preferred.

Examples of therapeutic agents include antiulcerants such as omeprazole, famotidine or ranitidine; antihypertensives such as amlodipine, valsartan, or losartan; beta blockers such as atenolol or propranolol; calcium channel blockers such as nitrendipine or verapamil; ace inhibitors such as enalapril or ramipril; angiotensin II inhibitors such as losartan potassium; potassium channel activators, such as nicorandil; diuretics and antidiuretics such as hydrochlorothiazide or triamterene; antianginals such as isosorbide dinitrate or diltiazem; coagulants such as conjugated menadione or haemocoagulase; anti-coagulants antithrombotics or antiplatelets such as tissue plasminogen activator or heparin; antiarrhythmics such as disopyramide or amiodarone; vasodilators such as digitoxin, digoxin or digitalin; penicillins such as piperacillin, or amoxycillin (optionally in combination with clavulanic acid); beta-lactam such as imipenem or meropenem; quinolones or fluoroquinolones such as nalidixic acid, levofloxacin or moxifloxacin; cephalosporins such as cefdinir or cefaclor; sulphonamides such as sulphametoxazole; aminoglycosides such as azithromicin or gentamicin; polymyxins such as polymyxin-b; tetracyclines such as doxycycline; macrolides such as erythromycin or clindamycin; oxazolidinones such as linezolid; antivirals, such as atazanavir, zidovudine, efavirenz, tenofovir, abacavir, tenofovir, lopinavir, acyclovir, valaciclovir, ozeltamivir; antimalarials, such as artesunate or mefloquine; antituberculars such as, isoniazid; streptomycin or pyrazinamide; anthelmintics and antiinfestives such as piperazine, pyrantel pamoate, or membendazole; antileprotics such as antiprotozoals; antiamoebics such as metronidazole; antifungals such as caspofungin, voriconazole, fluconazole; antiallergics such as mometazone, fexofenadine, terfenadine, or cetirizine; skeletal muscle relaxants such as tizanidine or baclofen; non steroidal anti-inflammatory drugs such as celecoxib, meloxicam, or ibuprofen; antineoplastic agents, such as nitrogen mustard compounds (e.g. cyclophosphamide), aziridines (e.g. thioepa), N-nitrosurea derivatives (e.g. lomustine), platinum compounds (e.g. oxaliplatin), procarbazine, dacarbazine methotrexate, adriamycin, mitomycin, ansamitocin, cytosine arabinoside, vineristine, daunorubicin hydrochloride, doxorubicin hydrochloride, epirubicin, mitoxantrone, bleomycin, aminoglutethimide, leuprolide acetate, goserelin, bicalutamide, tamoxifen citrate, trilostane, asparaginase (L-asparaginase), etoposide, interferon α-2a, interferon α-2b, teniposide (VM-26), vinblastine sulfate (VLB), vincristine sulfate, paclitaxel, docetaxel, camptothecin, irinotecan, methotrexate, adriamycin, arabinosyl, hydroxyurea; folic acid antagonists such as aminopterin, methotrexate, permetrexed; antagonists of nucleoside analogs such as gemcitabine, capecitabine, mercaptopurine, tioguanine, fluorouracil or cytarabine; tyrosine kinase inhibitors such as imatinib sorafenib, antibodies such as rituximab, cetuximab, erlotinib, trastuzumab or bevacizumab; aromatase inhibitors such as anastrozole or letrozole; narcotics, opiates or sedatives such as fentanyl citrate, flurazepam hydrochloride, pentobarbital, temazepam or triazolam; local or general anaesthetics such as sevoflurane, procaine, tetracaine or droperidol; neuromuscular blockers such as atracurium mesylate; therapeutics for the hormonal system, such as growth hormone, melanocyte stimulating hormone, estradiol, beclomethasone dipropionate, betamethasone, cortisone acetate, dexamethasone; drugs against acromegaly, such as somatostatin; drugs against Alzheimer disease, such as memantine, donepezil, rivastigmine; drugs against anemia, such as erythropoietin; drugs against attention-deficit hyperactivity disorder such as methylphenidate and atomoxetine; drugs agains benign prostatic hyperplasia such as tamsulosin, finasteride, alfuzosin; drugs against bleeding such as coagulation factor VII, factor VIII; drugs against diabetes such as insulin or glimepiride; drugs against hepatitis C such as pegylated interferon alfa 2a, pegylated interferon alfa-2b, drugs against infertility such as follitropin alfa and follitropin beta; drugs against multiple sclerosis such as glatiramer, interferon beta-1a or interferon beta-1b; drugs agaist osteoporosis such as alendronate; drugs against respiratory syncytial virus such as palivizumab; drugs against rheumatoid arthritis such as infliximab, etanercept or adalimumab; drugs agains schizophrenia such as risperidone or olanzapine; or drugs against transplant rejection such as tacrolimus, mycophenolate or ciclosporin.

The term "gas-filled microvesicles" includes any structure comprising bubbles of gas of micronic or nanometric size (e.g. from 0.1 to 10 µm, typically from 1 to 8 µm) surrounded by an envelope or layer (including film-form layers) of a stabilizing material. The term includes in particular what is known in the art as gas-filled liposomes, microbubbles, microspheres, microballoons or microcapsules. The stabilizing material can be any material typically known in the art including, for instance, surfactants, lipids, sphingolipids, oligolipids, glycolipid, phospholipids, proteins, polypeptides, carbohydrates, and synthetic or natural polymeric materials. Preferred gas-filled microvesicles are those where the interactions among the different components forming the envelope are of the non-covalent type, typically including dipole-dipole interactions, hydrogen bonding, hydrophilic or hydrophobic interactions, van der Waal's forces and combinations thereof, particularly hydrophobic interactions. Typically, gas-filled microvesicles are employed in CEUS (contrast enhanced Ultrasound) imaging. In addition, these microvesicles can also be employed in therapeutic treatments, such as for instance ultrasound mediated drug delivery as illustrated herein.

The term "microbubbles" includes aqueous suspensions in which the bubbles of gas are bounded at the gas/liquid interface by a very thin envelope (film) involving a stabilizing amphiphilic material disposed at the gas to liquid interface (sometimes referred to in the art as an "evanescent" envelope). Microbubble suspensions can be prepared by contacting a suitable precursor thereof, such as powdered amphiphilic materials (e.g. freeze-dried preformed liposomes or freeze-dried or spray-dried phospholipid solutions) with air or other gas and then with an aqueous carrier, while agitating to generate a microbubble suspension which can then be administered, preferably shortly after its preparation. Examples of aqueous suspensions of gas microbubbles, of precursors and of the preparation thereof are disclosed, for instance, in Ref. 3, Ref. 4, Ref. 5, Ref. 6, and Ref. 7, which are here incorporated by reference in their entirety.

The terms "microballoons" or "microcapsules" include suspensions in which the bubbles of gas are surrounded by a solid material envelope of a lipid or of natural or synthetic polymers. Examples of microballoons and of the preparation thereof are disclosed, for instance, in Ref. 8 and Ref. 9.

The term "liposome" includes within its meaning substantially spherical aggregations of amphiphilic compounds, including lipid compounds, typically in the form of one or more concentric bi-layers of molecules with a non-covalent interaction among them.

The term "precursor thereof" includes any composition which, upon reconstitution with an aqueous carrier is capable of producing a suspension of a desidered molecular assembly. In particular when referred to a precursor of a gas-filled microvesicle, the expression includes any composition which, upon reconstitution with an aqueous carrier in the presence of a gas, is capable of producing a suspension of gas-filled microvesicles as defined above. Said precursor compositions typically comprise any of the above-cited stabilizing materials in dry powdered form (e.g. freeze-dried or spray-dried) capable of forming gas-filled microvesicles upon shaking an aqueous suspension thereof in the presence of a gas. Similarly, a precursor of a liposome includes suitable (amphiphilic) materials in dried powdered form which, upon reconstitution with an aqueous carrier, are capable of forming a liposome suspension.

The phrase "envelope-forming moiety" includes any moiety which is capable of participating to the formation of the stabilizing envelope of liposomes or gas-filled microvesicles. Said moiety is preferably an amphiphilic material, preferably comprising a phospholipid.

The expression "MRI contrast agent" refers to contrast agent comprising a compound, composition or formulation which is responsive to magnetic resonance, such as paramagnetic metal ions or a magnetite particles, as well as supramolecular constructs comprising said compounds such as, for instance, liposomes or micelles.

The expression "X-ray contrast agent" or "CT-contrast agents" refers to those contrast agents capable of enhancing the imaging of X-ray of computer tomography analysis including, for instance, iodinated compounds, in particular non-ionic (such as iopamidol or iomeprol, from Bracco Imaging), barium sulfate or Gold nanoparticles.

The expression "optical imaging agent" refers to compounds or formulations capable of enhancing the imaging in various optical imaging techniques, including Diffused Optical Tomography (DOT), Optical Projection Tomography (OPT), Near-Infrared Fluorescence imaging (NIR) or Bioluminescence imaging (BLI). Contrast agents for optical imaging include organic fluorophores (e.g. fluorescent proteins) and inorganic fluorescent semiconductor nanocrystals or quantum dots (see e.g. Ref. 10).

The expression "nuclear imaging agent" refers to compounds or formulations capable of enhancing the imaging in nuclear imaging, which includes Positron-Emission Tomography (PET) and Single Photon Emission Tomography (SPECT). The first imaging technique uses a positron emitting isotope such as $^{11}C$, $^{13}N$, $^{15}O$, $^{18}F$, $^{68}Ca$, $^{94m}Tc$ (see e.g. Ref. 11). The second imaging technique uses a gamma emitting isotope such as $^{133}Xe$, $^{99m}Tc$, $^{123}I$, $^{201}Tl$, $^{111}In$ and $^{67}Ca$. All these agents can be formulated using nanoparticles as carrier system such as liposomes, (see e.g. Ref. 12 and Ref. 13).

The term "polymer" refers to macromolecules comprising repeating structural units (monomers), e.g. from 5 up to one million or more monomers, connected by covalent chemical bonds. Polymers may be synthetic, semi-synthetic or naturally occurring, and comprise homopolymers (i.e. comprising the same repeating unit) or copolymers (i.e. comprising at least two different monomers). Copolymers can be periodic copolymers (e.g. where monomers A and B are arranged in a repeating sequence such as A-B-A-B-B-A-A-A-A-B-B-B), or random (or statistical) copolymers having random sequences of monomers A and B. Block copolymers typically comprise two or more homopolymer subunits linked to each other by covalent bond or a junction block. Block copolymers with two or three distinct blocks are called di-block copolymers (AAAAA-BBBBB) and tri-block copolymers (AAAAA-BBBBB-AAAAA), respectively. Polymers can be linear (with a single main chain) or branched (with one or more lateral chains attached to the main chain). The chain of the polymer containing the repeating units is generally identified as the "polymer backbone", while the units disposed at respective terminal ends of the chain are generally identified as "terminal groups".

The expression "hydrophilic polymer" includes polymers having affinity for water, typically containing polar groups in their backbone such as, for instance, —O—, —NH—, —SH—, —CO— or any combination thereof. Examples of hydrophilic polymers include poly($C_2$-$C_3$)alkyl-oxides (e.g. PEG or PPG), polysaccharides (e.g. dextran), polyamino acids, semisynthetic peptides and polynucleotides.

Anti-Polymer Antibodies

In the following of the specification the term "anti-polymer antibody", is intended to comprise within its meaning any antibody which is capable of recognizing a polymer, or a portion thereof, as an antigen and of selectively binding to it, particularly when said polymer is comprised in the envelope of a liposome or of a gas-filled microvesicle as illustrated herein.

The term antibody as used herein includes polyclonal antibodies, monoclonal antibodies, natural antibody fragments, recombinant antibody fragments and multispecific antibodies. The term further comprises antigen binding fragments of proteins designed to compete with antibodies for specific binding, such as affibodies.

Anti-polymer antibodies can be produced by any method known in the art (e.g. immunisation of wild-type or transgenic animals, isolation from human patients sera, and screening of antigen-binding fragment libraries). Antibodies referred hereto can be from any species and any class including, mammal IgG, M, A and E. They can follow the native antibody sequence of the source specie or amino acid variant thereof, including so-called "humanized" or PRIMATIZED™ antibodies.

Antibodies are typically identified in the art as immunoglobulins (Ig), a family of multimeric glycoproteins produced by the immune system in response to pathogens invasion. They are composed of an antigen-binding portion (Fab) and an effector function (Fc). Mouse IgG, for instance, is a Y-shaped heterotetramer of two identical heavy chains (H) and two identical light chains (L). Each light chain is linked to a heavy chain by hydrophobic interactions and often a covalent disulfide bond, while the number of disulfide linkage between heavy chains varies among antibody subclasses. Each heavy and light chain also has regularly spaced intrachain disulfide bridges involved in the stabilisation of the globular folding called "immunoglobulin domain". The amino terminal domain of each chain is said "variable" ($V_H$ and $V_L$ as opposed to "constant" domains $C_{H1}$, $C_{H2}$, $C_{H3}$ and $C_L$) because it differs extensively in sequence among antibodies, this diversity being the basis of binding specificity. However the variability is not evenly distributed throughout the variable domains of antibodies. It is concentrated in three segments called Complementarity Determining Regions (CDRs), whereas the most conserved portions of variable domains are called the Framework Regions (FRs).

The expression "polyclonal antibodies" typically include different antibodies directed against different determinants (epitopes) of a same antigen. The preparation of polyclonal antibodies is well-known to those skilled in the art and described in a number of reference books, such as, for instance in Ref. 14.

The expression "monoclonal antibody" refers to an antibody obtained from a population of substantially homogenous antibodies, i.e. the individual antibodies comprising the population are identical except for possible naturally occurring mutations that may be present in minor amounts. Monoclonal antibodies are highly specific, being directed against a single antigenic determinant. Monoclonal antibodies are often identified as "intact" monoclonal antibodies, where the term "intact" indicates that the antibody comprises all its naturally occurring portions (antigen binding and effector) and is under its natural form (e.g. monomeric bivalent for IgG, dimeric tetravalent for IgA, and pentameric decavalent for IgM), whether it has been produced by the hybridoma method (see e.g Ref. 15), by recombinant DNA technology (see e.g. Ref. 16), by direct cloning of the various amino acid chains (see e.g. Ref. 17), by immortalisation of B-cells (see e.g. Ref. 18) or by screening of antibody libraries (see e.g. Ref. 19).

The expression "natural antibody fragments" refers to those compounds which comprise a portion of an antibody, preferably the antigen binding region, which retains some ability to selectively bind with its antigen. The term "natural" specifies that they are obtained by enzymatic or chemical cleavage of intact antibodies. Examples of natural antibody fragments include Fab, Fab' and F(ab')$_2$.

The term "Fab" identifies the fragment that contains a monovalent antigen-binding fragment of an antibody molecule. A Fab fragment can be produced by digestion of the whole antibody with the enzyme papain to yield an intact light chain and a portion of one heavy chain.

The term "Fab'" (or "Fab prime") identifies the fragment of an antibody molecule that can be obtained by treating the whole antibody with pepsin, followed by reduction, to yield an intact light chain and a portion of the heavy chain. Two Fab' fragments are obtained per antibody molecule. Fab' fragments differ from Fab fragments by the addition of a few residues at the carboxyl terminus of the heavy chain CH1 domain including one or more cysteines from the antibody hinge region.

The term "(Fab')$_2$" identifies the fragment of an antibody that can be obtained by treating the whole antibody with the enzyme pepsin, without subsequent reduction. (Fab')$_2$ is a dimer of two Fab' fragments held together by two disulfide bonds.

Methods of making antibody fragments are well known in the art. These methods are described, for example, in Ref. 14.

"Recombinant antibody fragments" are synthesised in vitro directly as small antibody portions. Examples of engineered antibody fragments include Fab, Fab' and F(ab')$_2$, Fv, scFv, Fd, $V_H$, $V_L$, CDR peptides, minibodies, multibodies, VhH and V-NAR.

The variable fragment "Fv" is comprised of a dimer of one heavy and one light chain variable domain in a tight, non-covalent association ($V_H$-$V_L$ dimer). It is the minimum antibody fragment that contains a complete antigen recognition and binding site. It is in this configuration that the three CDRs of each variable domain interact to define an antigen binding site on the surface of the $V_H$-$V_L$ dimer. Alternatively, the variable chains can be linked by an intermolecular disulfide bond or cross-linked by chemicals such as glutaraldehyde.

"scFv" is the single chain variable fragment and is a genetically engineered molecule containing the variable region of the light chain ($V_L$) and the variable region of the heavy chain ($V_H$) linked to each other by a suitable polypeptide linker, such as a genetically fused single chain molecule. The polypeptide linker between the domains enables the scFv to form the desired structure for antigen binding (see e.g. Ref. 20).

"Fd" is the part of the immunoglobulin heavy chain comprising of the two amino-terminal domains ($V_H$ and $C_{H1}$). It can be produced by in vitro expression systems together with a light chain in order to generate recombinant Fab, as disclosed for instance in Ref. 21.

Collectively, the six CDRs (three for each variable region) confer antigen binding specificity to the antibody. However, even a single variable domain (or half of an Fv comprising only three CDRs specific for an antigen) has the ability to recognize and bind antigen, although at a lower affinity than the entire binding site. Separately they exhibit very low solubility due to exposed hydrophobic residues. However they can be combined to form Fv.

The expression "CDR peptides" includes minimal recognition units coding for a single complementarity-determining region. CDR peptides can be obtained by constructing genes encoding the CDR of an antibody of interest. Such genes are prepared, for example, by using the polymerase chain reaction to synthesize the variable region from RNA of antibody-producing cells. Alternatively, CDR peptides can be obtained by screening phage display or ribosome display libraries (see e.g. Ref. 22).

The term "Minibodies" refers to small versions of a whole antibody which encode, in a single chain, the essential elements of a whole antibody. It comprises the $V_L$ and $V_H$ domains of a native antibody fused to the hinge region and $C_{H3}$ domain. They are expressed by host cells transformed with minibody genes (see e.g. Ref. 23 or Ref. 24).

The term "multibodies" refers to multivalent constructs with several antigen-binding sites derived from antibodies, e.g. diabodies, bis-scFV, triabodies, tetrabodies. "Diabodies", for instance, are small antibody fragments with two antigen-binding sites, which fragments comprise a heavy chain variable domain (VH) connected to a light chain variable domain (VL) in the same polypeptide chain (VH-VL). By using a linker that is too short to allow pairing between the two domains on the same chain, the domains are forced to pair with the complementary domains of another chain and create two antigen-binding sites. Diabodies are described in more detail, for example, in Ref. 25 or Ref. 26. Bis-scFv has an overall structure close to diabodies, except that it is composed of only one polypeptide comprising four variable domains (see e.g. Ref. 25).

The terms "VhH" and "V-NAR" refer to the single high affinity V-like domain of camelid and shark Ig, respectively (see e.g. Ref. 27). Unlike rodent or primate $V_H$ domains, those are soluble fragments, while llama VhH domains appear to be only minimally immunogenic.

A review of recombinant antibody fragments can be found, for instance, in Ref. 27, while methods for producing such recombinant antibody fragments are described, for example, in Ref. 28 or Ref. 29.

Anti-polymer antibodies can virtually be generated against any type of polymer antigen. For instance, polyclonal and monoclonal antibodies have been generated against numerous natural, synthetic and semi-synthetic polymers, such as, anti-hemagglutinin, anti-HIV gp120, anti-phosphoprotein, anti-DNA, anti-galactan, anti-dextran, anti-polylysine, anti-polyarginine, anti-polyacrylamide, anti-polyvinylpyrrolidone and anti-polyethylene glycol antibodies, as illustrated for instance in Ref. 30.

Preferred antibodies are those which recognizes and specifically bind to a hydrophilic polymer including, for instance, polymers or copolymers comprising oxyethylene repeating units in their backbone, such as polyethylenglycol (PEG, also identified as "polyethylene oxide"—PEO, or "polyoxyethylene"—POE—in the art) and derivatives thereof, polymers or copolymers containing oxypropylene repeating units, such as polypropylenglycol (PPG, also identified as "polypropylene oxide"—PPO, or "polyoxypropylene"—POP—in the art) and derivatives thereof, polysaccharides (e.g. dextran), polyamino acids (e.g. polylysine), poly- or oligo-nucleotides or semi-synthetic peptides. More preferred antibodies are those which are capable of recognizing and specifically binding to polymers or copolymers comprising repeating oxyethylene units in their backbone, such as PEG or copolymers of ethylene oxide and propyleneoxide (e.g. block copolymers of PEG and PPG). Particularly preferred are those antibodies which recognizes and bind to a polymer comprising repeating oxyethylene units (e.g. PEG) and terminated with a methoxy group (e.g. mPEG, i.e. a methoxy-terminated PEG).

For instance, antibodies capable of specifically binding to mPEG are particularly advantageous as they can be employed for specifically binding supramolecular assemblies containing said mPEG, which can be comprised in formulations containing also non-methoxylated PEG polymers (for instance, PEG without terminal methoxy group is often used as cryoprotectant material in the preparation of lyophilized precursors of gas-filled microvesicles or of liposomes).

Anti-PEG antibodies are well known in the art and are described, for instance, in Ref. 31 or Ref. 32 both herein incorporated by reference. Commercial anti-PEG antibodies specific for binding to PEG-backbone (i.e. to sequences of repeating oxyethylene units in the backbone of the polymer) are available as AGP3 and E11 (Institute of Biomedical Sciences, Academia Sinica, Taipei, Taiwan), while antibodies specific for binding to PEG polymers terminated with a methoxy group are available as antibody PEG-B-47 (Epitomics Inc. USA).

Targeting Ligands

In order to allow an effective binding of the polymer-containing liposome or gas-filled microvesicle to the desired body region or tissue, the anti-polymer antibody is associated with a suitable component capable of binding to said specific body region or tissue. Said component thus comprises a targeting moiety capable of binding to a corresponding target on said specific body region or tissue, e.g. a receptor expressed in the specific body region or tissues. The term "targeting ligand" as used herein includes any compound, moiety or residue having, or being capable of promoting, a targeting activity towards tissues and/or receptors in vivo. Targets with which a targeting ligand may be associated include tissues such as, for instance, myocardial tissue (including myocardial cells and cardiomyocytes), membranous tissues (including endothelium and epithelium), laminae, connective tissue (including interstitial tissue) or tumors; blood clots; and receptors such as, for instance, cell-surface receptors for peptide hormones, neurotransmitters, antigens, complement fragments, immunoglobulins and cytoplasmic receptors for steroid hormones. Because of their mean size, liposomes and gas-filled microvesicle have a general tendency to remain within the intravascular compartment; it is thus preferred that the targeting site is most preferably endoluminal in location. Accordingly, molecular targets are preferably associated with endothelial cells of the vascular endothelial lining. These targets can be either at the surface of the endothelial cells or integrated within the endothelial cell membrane.

Examples of suitable targeting ligands include, for instance, proteins, including antibodies, antibody fragments, receptor molecules, receptor binding molecules, glycoproteins and lectins; peptides, including oligopeptides and polypeptides; peptidomimetics; saccharides, including mono and polysaccharides; vitamins; steroids, steroid analogs, hormones, cofactors, bioactive agents including substituted small molecules and genetic material, including nucleosides, nucleotides and polynucleotides and mimetics thereof, such as peptide nucleic acids.

Examples of suitable targets and targeting ligands are disclosed, for instance, in Ref. 33, which is herein incorporated by reference.

Examples of suitable specific targets to which a targeted microvesicle of the invention can be directed are, for instance, fibrin and the GPIIbIIIa receptor on activated platelets. Fibrin and platelets are generally present in "thrombi", i.e. coagula which may form in the blood stream and cause a vascular obstruction. In addition, fibrin may also be associated with various tumoral processes. Preferred binding peptides specific for fibrin-targeting are disclosed, for instance, in Ref. 34 here incorporated by reference. Further preferred binding peptides specific for fibrin-targeting are also disclosed in Ref. 35 and Ref. 36, which are also herein incorporated by reference.

Other examples of important targets include receptors in vulnerable plaques and tumor specific receptors, such as kinase insert domain receptor (KDR) and VEGF (vascular endothelial growth factor)/KDR complex. Examples of binding peptides suitable for targeting KDR or VEGF/KDR complex are disclosed, for instance in Ref. 37, Ref. 38, Ref. 39 and Ref. 40, all herein incorporated by reference. Other examples of tumor specific ligands are, for instance, transferrin, folic acid, arginine-glycine-aspartic acid sequence (RGD), NRG sequence (for targeting aminopeptidase expressed on newly formed vessels) or GA3 peptide sequence (target Tie2 receptor involved in tumor angiogenesis), Tuftsin-like sequences (targeting NRP-1 receptor as described in Ref. 41).

According to an embodiment of the invention, the targeting ligand is an antibody where the term antibody includes polyclonal antibodies, monoclonal antibodies, natural antibody fragments, recombinant antibody fragments and multispecific antibodies as defined above, as well as antigen binding fragments thereof (e.g. affibodies). Examples of suitable antibodies, and of their respective potential target, where available, are illustrated in the following table.

| Antibody | target | Comment/area of use |
|---|---|---|
| Anti ICAM-1/ CD54 | Intercellular Adhesion Molecule-1 | Endothelial cells activation |
| Anti ICAM-2 | Intercellular Adhesion Molecule-2 | as above |
| Anti CD62E | L-Selectin | as above |
| Anti CD62P | P-Selectin | as above |
| Anti CD31 | PECAM-1 | as above |
| Anti-TM/CD141 | Thrombomodulin | as above |
| Anti-VCAM-1/ CD106 | vascular cell adhesion molecule-1 | as above |
| Anti CD105 | Endoglin | marker of angiogenic endothelial cells |
| Anti Endocan | Endothelial cell specific molecule-1 (ESM-1) | as above |
| Anti-KDR/Flk-1 | Vascular endothelium growth factor Receptor-2 | as above |
| Anti-Flt-1 | Vascular endothelium growth factor Receptor-1 | as above |
| Anti-Nucleolin | | as above |
| Anti-TEM1 | Tumor endothelial marker 1/endosialin | as above |
| Anti-TEM5 | Tumor endothelial marker 5 | as above |
| Anti-TEM7 | Tumor endothelial marker 7 | as above |
| Anti-TEM8 | Tumor endothelial marker 8 | as above |
| Anti-TF | Tissue Factor | as above |
| Anti PSMA | Prostate Specific Membrane Antigen | as above |
| Anti-CXCR4 | | marker of angiogenic endothelial cells |
| Anti-NRP1 | Neuropilin-1 | marker of angiogenic endothelial cells |
| Integrins, (e.g. VLA-1, VLA-2, VLA-3, VLA-4, VLA-5, VLA-6, α7 β1, αvβ3, α5β3 LFA-1, Mac-1, D41a) | | endothelial cell marker |
| Anti-VE-cadherin (CD144) | | as above |
| Anti-vWF | von Willebrand factor | as above |
| Anti CD34 | CD34/gp105-120 | as above |

Association of Anti-Polymer Antibody with Targeting Ligand

Useful targeting construct for use in the present invention can be represented by the following general formula:

$$(TL)_n Z(APA)_m$$

where

TL represents a targeting ligand as above defined, optionally functionalized with a moiety capable of reacting with or of forming the linker Z;

APA represents an anti-polymer antibody as above defined, optionally functionalized with a moiety capable of reacting with or forming the linker Z;

Z represents a bi- or multi-functional linker selected from a covalent bond; a linking moiety; a chelating moiety; a binding protein (e.g. avidin or streptavidin); or a supramolecular vector, such as a micelle, a liposome or a nanoparticle; and n and m are integers varying independently from 1 to 100,000.

For instance when Z is a covalent bond (i.e. a bi-functional linker), TL and APA are suitably modified to react with each other (thus forming the linker Z as a covalent bond) and m and n are both 1.

When Z is streptavidin (a tetrafunctional linker), TL and APA are suitably modified to interact with the linker (in particular, a biotin moiety is introduced in the respective structures of TL and APA), m can be 1, 2 or 3 while n can be 3, 2 or 1, respectively (the total m+n being 4).

When Z is multifunctional linker such as a micelle or liposome, TL and APA are modified to interact with the linker (e.g. they can be linked to a molecule forming the micelle or liposome) and both n and m may vary from 1 to 100,000, depending on the composition of the linker and its size.

The anti-polymer antibody can be associated with the targeting ligand according to different procedures and methodologies, to provide the desired targeting construct.

In a first embodiment, the anti-polymer antibody is covalently bound to a targeting ligand. In this case, the APA and the TL are preferably generated as recombinant fusion protein such as diabodies or bispecific bis-scFv. Bispecific antibodies can also be produced by fusing two hybridomas (hybrid-hybridoma) or by joining two reduced antibody fragments via disulfide bonds. Alternatively bispecific antibodies can be generated by chemical coupling of two different antibodies using heterobifunctional or homobifunctional linkers, multivalent functionalised polymer such as 4-arm PEG-maleimide (CreativePegWorks, USA) or by introducing directional coupling groups, such as those available in the "Bioconjugate toolkit reagents" (Pierce, Switzerland). For instance, an APA can be modified by introducing hydrazine moieties into its structure, e.g. by reacting the component with succinimidyl 4-hydrazinonicotinate acetone hydrazone. Separately, a TL (e.g. a targeting antibody, or a fragment thereof) is modified to introduce aldehyde groups into its structure, e.g. by reacting it with succinimidyl 4-formylbenzoate. The so modified compounds are then reacted in equimolar ratio at room temperature for several hours to form covalently bound bispecific conjugates. If desired, heterodimers can be separated from unreacted compounds and/or multimers by gel filtration chromatography. Of course, the above procedure can be similarly performed by introducing hydrazine group into a targeting ligand (e.g. a targeting antibody, or a fragment thereof) and by to introducing aldehyde groups into the structure of the anti-polymer antibody. Similarly, instead of diabody, bifunctional APAs and TLs can be suitably modified to produce a tetrabody, where two APAs are linked to two TLs.

In a preferred embodiment, the anti-polymer antibody is associated non-covalently with a targeting ligand (e.g. in the form of a supramolecular assembly, such as micelles, nanoparticles or liposomes).

Figure 1:
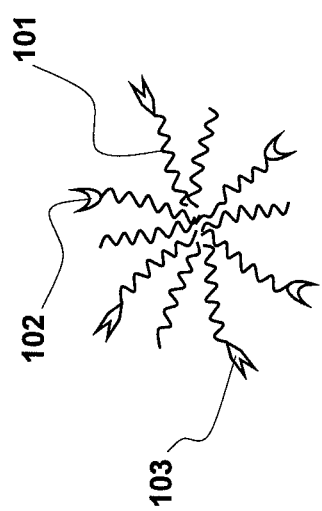

For instance, the antibody and the targeting ligand can be associated non-covalently in the form of micelles, as illustrated in FIG. 1. To this end, an amphiphilic compound 101 (e.g. a phospholipid) is covalently bound to the anti-polymer antibody 102 while another (or the same) amphiphilic compound is bound to the desired targeting ligand 103. The two amphiphilic compounds containing the respective additional component are then admixed in an aqueous carrier, to obtain the targeting construct in the form of a micellar assembly.

Alternatively, the antibody and the targeting ligand can be associated non-covalently in the form of liposomes as illustrated in FIG. 2. For instance, similarly to the above procedure, an APA and a TL (indicated as 202 and 203, respectively) can be covalently bound to respective amphiphilic compounds 201, which will then be included into the liposome's envelope 204 (formed e.g. by the same and/or by different amphiphilic compound compounds). Advantageously, the use of micellar structures, and particularly of liposomes, allows enhancing the amount of binding sites for the polymer-containing liposomes or microvesicles, particularly in those cases where the amount of targeting sites in the region of interest is relatively low.

Figure 3:
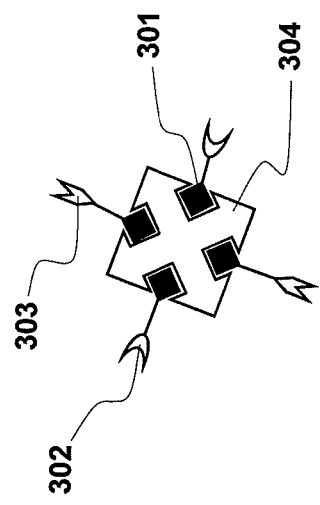

Alternatively, said non-covalent association can be based on a biological specific affinity interaction (e.g. streptavidin-biotin binding) as illustrated in FIG. 3. For instance, a targeting ligand 303 can be modified by introducing a biotin moiety 301 into its structure (e.g. by incubating a phosphate buffer suspension of a targeting antibody in the presence of a solution containing reactive biotin). Similarly, also an anti-polymer antibody 302 can be modified in a similar manner, to obtain a biotinylated anti-polymer antibody. A mixture of the two biotinylated antibodies is then reacted with a suspension containing streptavidin 304 (capable of binding with four biotin moieties), to obtain the desired bi-specific construct schematically represented in FIG. 3. If desired, the construct comprising the targeting ligand and the APA may advantageously also comprise a therapeutic agent. For instance, said therapeutic agent can be included within a liposome composition.

In an alternative embodiment, it is also possible to prepare mixtures of different (i.e. two or more) targeting constructs comprising different targeting ligands associated with the anti-polymer antibody.

For instance, this can be obtained by simply admixing two or more different preparations of targeting constructs (either with covalent or non-covalent binding between the antibody and the targeting ligand) prepared as described above. Alternatively, the mixture can be obtained by using two or more targeting ligands (admixed with an anti-polymer antibody) for preparing a supramolecular vector (e.g. a micelle, liposome) or by using two or more different biotinylated targeting ligands (admixed with a biotinylated anti-polymer antibody) for the preparation of a biotin-streptavidin targeting construct, according to the procedures illustrated above.

Gas-Filled Microvesicles

Gas-filled microvesicles according to the invention can be any microvesicle known in the art, including gas-filled microbubbles, microcapsules and microballoons.

Preferred microvesicles are gas-filled microbubbles, i.e. microvesicles which are generally stabilized by one or more amphiphilic component. Amphiphilic components suitable for forming a stabilizing envelope of microbubbles comprise, for instance, phospholipids; lysophospholipids; fatty acids, such as palmitic acid, stearic acid, arachidonic acid or oleic acid; lipids bearing polymers, such as chitin, hyaluronic acid, polyvinylpyrrolidone or polyethylene glycol (PEG), also referred as "pegylated lipids"; lipids bearing sulfonated mono- di-, oligo- or polysaccharides; cholesterol, cholesterol sulfate or cholesterol hemisuccinate; tocopherol hemisuccinate; lipids with ether or ester-linked fatty acids; polymerized lipids; diacetyl phosphate; dicetyl phosphate; ceramides; polyoxyethylene fatty acid esters (such as polyoxyethylene fatty acid stearates), polyoxyethylene fatty alcohols, polyoxyethylene fatty alcohol ethers, polyoxyethylated sorbitan fatty acid esters, glycerol polyethylene glycol ricinoleate, ethoxylated soybean sterols, ethoxylated castor oil or ethylene oxide (EO) and propylene oxide (PO) block copolymers; sterol aliphatic acid esters including, cholesterol butyrate, cholesterol iso-butyrate, cholesterol palmitate, cholesterol stearate, lanosterol acetate, ergosterol palmitate, or phytosterol n-butyrate; sterol esters of sugar acids including cholesterol glucuronides, lanosterol glucoronides, 7-dehydrocholesterol glucoronide, ergosterol glucoronide, cholesterol gluconate, lanosterol gluconate, or ergosterol gluconate; esters of sugar acids and alcohols including lauryl glucoronide, stearoyl glucoronide, myristoyl glucoronide, lauryl gluconate, myristoyl gluconate, or stearoyl gluconate; esters of sugars with aliphatic acids including sucrose laurate, fructose laurate, sucrose palmitate, sucrose stearate, glucuronic acid, gluconic acid or polyuronic acid; saponins including sarsasapogenin, smilagenin, hederagenin, oleanolic acid, or digitoxigenin; glycerol or glycerol esters including glycerol tripalmitate, glycerol distearate, glycerol tristearate, glycerol dimyristate, glycerol trimyristate, glycerol dilaurate, glycerol trilaurate, glycerol dipalmitate; long chain alcohols including n-decyl alcohol, lauryl alcohol, myristyl alcohol, cetyl alcohol, or n-octadecyl alcohol; 6-(5-cholesten-3β-yloxy)-1-thio-β-D-galactopyranoside; digalactosyldiglyceride; 6-(5-cholesten-3β-yloxy)hexyl-6-amino-6-deoxy-1-thio-β-D-galactopyranoside; 6-(5-cholesten-3β-yloxy)hexyl-6-amino-6-deoxyl-1-thio-β-D-mannopyranoside; 12-(((7'-diethylaminocoumarin-3-yl)carbonyl)methylamino) octadecanoic acid; N-[12-(((7'-diethylaminocoumarin-3-yl)

carbonyl)methylamino)octadecanoyl]-2-aminopalmitic acid; N-succinyldioleylphosphatidylethanolamine; 1,2-dioleyl-sn-glycerol; 1,2-dipalmitoyl-sn-3-succinylglycerol; 1,3-dipalmitoyl-2-succinylglycerol; 1-hexadecyl-2-palmitoylglycerophosphoethanolamine or palmitoylhomocysteine; alkylamines or alkylammonium salts, comprising at least one ($C_{10}$-$C_{20}$), preferably ($C_{14}$-$C_{18}$), alkyl chain, such as, for instance, N-stearylamine, N,N'-distearylamine, N-hexadecylamine, N,N'-dihexadecylamine, N-stearylammonium chloride, N,N'-distearylammonium chloride, N-hexadecylammonium chloride, N,N'-dihexadecylammonium chloride, dimethyldioctadecylammonium bromide (DDAB), hexadecyltrimethylammonium bromide (CTAB); tertiary or quaternary ammonium salts comprising one or preferably two ($C_{10}$-$C_{20}$), preferably ($C_{14}$-$C_{18}$), acyl chain linked to the N-atom through a ($C_3$-$C_6$) alkylene bridge, such as, for instance, 1,2-distearoyl-3-trimethylammonium-propane (DSTAP), 1,2-dipalmitoyl-3-trimethylammonium-propane (DPTAP), 1,2-oleoyl-3-trimethylammonium-propane (DOTAP), 1,2-distearoyl-3-dimethylammonium-propane (DSDAP); and mixtures or combinations thereof.

According to a preferred embodiment, at least one of the compounds forming the microbubbles' envelope is a phospholipid, optionally in admixture with any of the other above cited materials. According to the present description, the term phospholipid is intended to encompass any amphiphilic phospholipid compound, the molecules of which are capable of forming a stabilizing film of material (typically in the form of a mono-molecular layer) at the gas-water boundary interface in the final microbubbles suspension. Accordingly, these materials are also referred to in the art as "film-forming phospholipids".

Amphiphilic phospholipid compounds typically contain at least one phosphate group and at least one, preferably two, lipophilic long-chain hydrocarbon group.

Examples of suitable phospholipids include esters of glycerol with one or preferably two (equal or different) residues of fatty acids and with phosphoric acid, wherein the phosphoric acid residue is in turn bound to a hydrophilic group, such a, for instance, choline (phosphatidylcholines—PC), serine (phosphatidylserines—PS), glycerol (phosphatidylglycerols—PG), ethanolamine (phosphatidylethanolamines—PE), inositol (phosphatidylinositol). Esters of phospholipids with only one residue of fatty acid are generally referred to in the art as the "lyso" forms of the phospholipid or "lysophospholipids". Fatty acids residues present in the phospholipids are in general long chain aliphatic acids, typically containing from 12 to 24 carbon atoms, preferably from 14 to 22; the aliphatic chain may contain one or more unsaturations or is preferably completely saturated. Examples of suitable fatty acids included in the phospholipids are, for instance, lauric acid, myristic acid, palmitic acid, stearic acid, arachidic acid, behenic acid, oleic acid, linoleic acid, and linolenic acid. Preferably, saturated fatty acids such as myristic acid, palmitic acid, stearic acid and arachidic acid are employed.

Further examples of phospholipid are phosphatidic acids, i.e. the diesters of glycerol-phosphoric acid with fatty acids; sphingolipids such as sphingomyelins, i.e. those phosphatidylcholine analogs where the residue of glycerol diester with fatty acids is replaced by a ceramide chain; cardiolipins, i.e. the esters of 1,3-diphosphatidylglycerol with a fatty acid; glycolipids such as gangliosides GM1 (or GM2) or cerebrosides; glucolipids; sulfatides and glycosphingolipids.

As used herein, the term phospholipids include either naturally occurring, semisynthetic or synthetically prepared products that can be employed either singularly or as mixtures.

Examples of naturally occurring phospholipids are natural lecithins (phosphatidylcholine (PC) derivatives) such as, typically, soya bean or egg yolk lecithins.

Examples of semisynthetic phospholipids are the partially or fully hydrogenated derivatives of the naturally occurring lecithins. Preferred phospholipids are fatty acids di-esters of phosphatidylcholine, ethylphosphatidylcholine, phosphatidylglycerol, phosphatidic acid, phosphatidylethanolamine, phosphatidylserine, phosphatidylinositol or of sphingomyelin.

Examples of preferred phospholipids are, for instance, dilauroyl-phosphatidylcholine (DLPC), dimyristoyl-phosphatidylcholine (DMPC), dipalmitoyl-phosphatidylcholine (DPPC), diarachidoyl-phosphatidylcholine (DAPC), distearoyl-phosphatidylcholine (DSPC), dioleoyl-phosphatidylcholine (DOPC), 1,2 Distearoyl-sn-glycero-3-Ethylphosphocholine (Ethyl-DSPC), dipentadecanoyl-phosphatidylcholine (DPDPC), 1-myristoyl-2-palmitoyl-phosphatidylcholine (MPPC), 1-palmitoyl-2-myristoyl-phosphatidylcholine (PMPC), 1-palmitoyl-2-stearoyl-phosphatidylcholine (PSPC), 1-stearoyl-2-palmitoyl-phosphatidylcholine (SPPC), 1-palmitoyl-2-oleylphosphatidylcholine (POPC), 1-oleyl-2-palmitoyl-phosphatidylcholine (OPPC), dilauroyl-phosphatidylglycerol (DLPG) and its alkali metal salts, diarachidoylphosphatidyl-glycerol (DAPG) and its alkali metal salts, dimyristoylphosphatidylglycerol (DMPG) and its alkali metal salts, dipalmitoylphosphatidylglycerol (DPPG) and its alkali metal salts, distearoylphosphatidylglycerol (DSPG) and its alkali metal salts, dioleoyl-phosphatidylglycerol (DOPG) and its alkali metal salts, dimyristoyl phosphatidic acid (DMPA) and its alkali metal salts, dipalmitoyl phosphatidic acid (DPPA) and its alkali metal salts, distearoyl phosphatidic acid (DSPA), diarachidoylphosphatidic acid (DAPA) and its alkali metal salts, dimyristoyl-phosphatidylethanolamine (DMPE), dipalmitoylphosphatidylethanolamine (DPPE), distearoyl phosphatidyl-ethanolamine (DSPE), dioleylphosphatidyl-ethanolamine (DOPE), diarachidoylphosphatidyl-ethanolamine (DAPE), dilinoleylphosphatidylethanolamine (DLPE), dimyristoyl phosphatidylserine (DMPS), diarachidoyl phosphatidylserine (DAPS), dipalmitoyl phosphatidylserine (DPPS), distearoylphosphatidylserine (DSPS), dioleoylphosphatidylserine (DOPS), dipalmitoyl sphingomyelin (DPSP), and distearoylsphingomyelin (DSSP), dilauroyl-phosphatidylinositol (DLPI), diarachidoylphosphatidylinositol (DAPI), dimyristoylphosphatidylinositol (DMPI), dipalmitoylphosphatidylinositol (DPPI), distearoylphosphatidylinositol (DSPI), dioleoyl-phosphatidylinositol (DOPI).

Particularly preferred phospholipids are DAPC, DSPC, DPPC, DMPA, DPPA, DSPA, DMPG, DPPG, DSPG, DMPS, DPPS, DSPS and Ethyl-DSPC. Most preferred are DPPG, DPPS and DSPC.

Mixtures of phospholipids can also be used, such as, for instance, mixtures of DPPE, DPPC, DSPC and/or DAPC with DSPS, DPPS, DSPA, DPPA, DSPG, DPPG, Ethyl-DSPC and/or Ethyl-DPPC.

In preferred embodiments, the phospholipid is the main component of the stabilizing envelope of microbubbles, amounting to at least 50% (w/w) of the total amount of components forming the envelope of the gas filled microbubbles. In some of the preferred embodiments, substantially the totality of the envelope (i.e. at least 90%) can be formed of phospholipids.

The phospholipids can conveniently be used in admixture with any of the above listed amphiphilic compounds. Thus, for instance, lipids such as cholesterol, ergosterol, phytosterol, sitosterol, lanosterol, tocopherol, propyl gallate or ascorbyl palmitate, fatty acids such as myristic acid, palmitic acid, stearic acid, arachidic acid and derivatives thereof or butylated hydroxytoluene and/or other non-phospholipid compounds can optionally be added to one or more of the foregoing phospholipids in proportions ranging from zero to 50% by weight, preferably up to 25%. Particularly preferred is palmitic acid.

In order to suitably interact with the anti-polymer antibody, the stabilizing envelope of the microbubble shall then comprise a polymer, preferably a hydrophilic polymer. Examples of suitable hydrophilic polymers include, for instance, polymers or copolymers comprising oxyethylene repeating units in their backbone, (such as PEG) and derivatives thereof, polymers or copolymers containing oxypropylene repeating units, such as PPG and derivatives thereof, polysaccharides (e.g. dextran), polyamino acids (e.g. polylysine), poly- or oligo-nucleotides or semi-synthetic peptides. Among these polymers, synthetic or semi-synthetic polymers are preferred, particularly preferred being polymers or copolymers comprising repeating oxyethylene units in their backbone, such as PEG or copolymers of ethylene oxide and propyleneoxide (e.g. block copolymers of PEG and PPG). According to a preferred embodiment, the polymer comprising repeating oxyethylene units is terminated with a methoxy group, i.e.:

$$-(O-CH_2-CH_2)_n-O-CH_3$$

where the free bound indicates the binding of the polymer with the microvesicle's envelope (or with a component thereof) and n is an integer indicating the number of repeating oxyethylene units of the polymer, which can vary from about 10 to about 2,000, preferably from about 20 to about 200 and more preferably from about 40 to about 160. Particularly preferred polymers are methoxy-terminated PEGs (mPEG).

The molecular weight of the polymer can vary from about 500 to about 100,000 Daltons, preferably from about 1,000 to about 10,000 Daltons. Particularly preferred is mPEG with a molecular weight of about 2,000 to 8,000 Daltons, more preferably of about 5,000 Daltons.

Said polymer is typically covalently bound to a compound compatible with the components of the stabilizing envelope of the microbubbles, preferably a compound comprising at least a hydrophobic portion therein (so as to hydrophobically interact with the other stabilizing compounds forming the envelope), preferably an amphiphilic compound such as, for instance, a phospholipid. Preferred examples of phospholipids containing a hydrophilic polymer are phosphatidylethanolamines (PE) modified with PEG ("PE-PEGs" in brief) i.e. phosphatidylethanolamines where the hydrophilic ethanolamine moiety is linked to a PEG molecule of variable molecular weight, such as DPPE-PEG (or DSPE-, DMPE-, DOPE-, DAPE or DLPE-PEG), i.e. DPPE (or DSPE, DMPE, DOPE, DAPE or DLPE) having a PEG polymer attached thereto. For example, DPPE-PEG5000 refers to DPPE having attached thereto a PEG polymer having a mean average molecular weight of about 5,000. Alternatively, the polymer can be bound to other amphiphilic lipid components such as, for instance, glycosylphosphatidylinositol (GPI), diacylglycerol, dialkyloxypropyl, ceramide or cholesterol, to form corresponding pegylated lipid derivatives. Other possible components comprising a hydrophilic polymer include non ionic surfactants, such as polyoxyethylene bis(imidazolyl carbonyl), polyoxyethylene fatty ethers (such as commercial Brij®), poloxamers (i.e. block copolymers of polyethylene oxide with polypropylene oxide, such as commercial Tween® or Pluronic®), polysorbates (i.e. derivatives of pegylated sorbitan reacted with fatty acids, such as commercial Triton®), polyethylene glycol sterates or polyoxyethylene stearates (such as commercial Myrj As observed by the Applicant, in order to allow an effective binding of the gas-filled microvesicles to the targeting construct containing the anti-polymer antibody, the molar amount of polymeric compound in the stabilizing envelope of the microvesicle shall preferably be of at least 0.05%, more preferably of at least 0.2% and even more preferably of at least 1%, with respect to the total molar amount of components forming said envelope. The presence of said plurality of polymer molecules on the surface of the microvesicle allows a multi-valent binding of the microvesicle to different APAs, thus improving the binding due to higher avidity.

On the other side, the Applicant has observed that excessive amounts of polymeric compound do not necessarily correspondingly enhance the binding efficacy of the microvesicles. Accordingly, the molar amount of polymeric compound is in general lower than about 15%, preferably lower than about 12% and more preferably lower than about 10%. In some preferred embodiments, particularly when an extensive (time) circulation of liposomes or gas-filled microvesicles in the vascular system is not desirable, it is preferred that the molar amount of polymeric compound is not higher than 4%, more preferably not higher than 2%.

The microbubbles of a composition according to the invention can be produced according to any known method in the art. Typically, the manufacturing method involves the preparation of a dried powdered material comprising an amphiphilic material as indicated above (including a polymer-bearing amphiphilic material), preferably by lyophilization (freeze drying) of an aqueous or organic suspension comprising said material.

For instance, as described in Ref. 3, film-forming amphiphilic compounds can be first converted into a lamellar form by any method employed for formation of liposomes. To this end, an aqueous solution comprising the film forming lipids and optionally other additives (e.g. viscosity enhancers, non-film forming surfactants, electrolytes etc.) can be submitted to high-speed mechanical homogenisation or to sonication under acoustic or ultrasonic frequencies, and then freeze dried to form a free flowing powder which is then stored in the presence of a gas. Optional washing steps can be performed before freeze drying.

According to an alternative embodiment (described for instance in Ref. 6) a film forming compound and a hydrophilic stabiliser (e.g. polyethylene glycol, polyvinyl pyrrolidone, polyvinyl alcohol, glycolic acid, malic acid or maltol) can be dissolved in an organic solvent (e.g. tertiary butanol, 2-methyl-2-butanol or $C_2Cl_4F_2$) and the solution can be freeze-dried to form a dry powder.

Preferably, as disclosed for instance in Ref. 7, a phospholipid (selected among those cited above, including a polymer-bearing phospholipid)) and a lyoprotecting agent (such as those previously listed, in particular carbohydrates, sugar alcohols, polyglycols, polyoxyalkylene glycols and mixtures thereof) can be dispersed in an emulsion of water with a water immiscible organic solvent (e.g. branched or linear alkanes, alkenes, cyclo-alkanes, aromatic hydrocarbons, alkyl ethers, ketones, halogenated hydrocarbons, perfluorinated hydrocarbons or mixtures thereof) under agitation. The emulsion can be obtained by submitting the aqueous medium and the solvent in the presence of at least one phospholipid to any appropriate emulsion-generating technique known in the art, such as, for instance, sonication, shaking, high pressure homogenization, micromixing, membrane emulsification, high speed stirring or high shear mixing. For instance, a rotor-stator homogenizer can be employed, such as Polytron®

PT3000. The agitation speed of the rotor-stator homogenizer can be selected depending from the components of the emulsion, the volume of the emulsion, the relative volume of organic solvent, the diameter of the vessel containing the emulsion and the desired final diameter of the microdroplets of solvent in the emulsion. Alternatively, a micromixing technique can be employed for emulsifying the mixture, e.g. by introducing the organic solvent into the mixer through a first inlet (at a flow rate of e.g. 0.05-5 mL/min), and the aqueous phase a second inlet (e.g. at a flow rate of 2-100 mL/min). Depending on the emulsion technique, the organic solvent can be introduced gradually during the emulsification step or at once before starting the emulsification step. Alternatively the aqueous medium can be gradually added to the water immiscible solvent during the emulsification step or at once before starting the emulsification step. Preferably, the phospholipid is dispersed in the aqueous medium before this latter is admixed with the organic solvent. Alternatively, the phospholipid can be dispersed in the organic solvent or it may be separately added the aqueous-organic mixture before or during the emulsification step. The so obtained microemulsion, which contains microdroplets of solvent surrounded and stabilized by the phospholipid material (and optionally by other amphiphilic film-forming compounds and/or additives), is then lyophilized according to conventional techniques to obtain a lyophilized material, which is stored (e.g. in a vial in the presence of a suitable gas) and which can be reconstituted with an aqueous carrier to finally give a gas-filled microbubbles suspension where the dimensions and size distribution of the microbubbles are substantially comparable with the dimensions and size distribution of the suspension of microdroplets.

A further process for preparing gas-filled microbubbles comprises generating a gas microbubble dispersion by submitting an aqueous medium comprising a phospholipid (and optionally other amphiphilic film-forming compounds and/or additives) to a controlled high agitation energy (e.g. by means of a rotor stator mixer) in the presence of a desired gas and subjecting the obtained dispersion to lyophilisation to yield a dried reconstitutable product. An example of this process is given, for instance, in Ref. 42, here enclosed by reference.

Spray drying techniques (as disclosed for instance in Ref. 43) can also be used to obtain a dried powder, reconstitutable upon contact with physiological aqueous carrier to obtain gas-filled microbubbles.

The dried or lyophilized product obtained with any of the above techniques will generally be in the form of a powder or a cake, and can be stored (e.g. in a vial) in contact with the desired gas, as a microvesicle precursor. The product is readily reconstitutable in a suitable physiologically acceptable aqueous liquid carrier, which is typically injectable, to form the gas-filled microbubbles, upon gentle agitation of the suspension. Suitable physiologically acceptable liquid carriers are sterile water, aqueous solutions such as saline (which may advantageously be balanced so that the final product for injection is not hypotonic), or solutions of one or more tonicity adjusting substances such as salts or sugars, sugar alcohols, glycols or other non-ionic polyol materials (eg. glucose, sucrose, sorbitol, mannitol, glycerol, polyethylene glycols, propylene glycols and the like).

According to an alternative embodiment, the gas-filled microvesicles of the invention can be microcapsules. Preferred examples of microcapsules are those having a stabilizing envelope comprising a polymer, preferably a biodegradable polymer, or a biodegradable water-insoluble lipid (such as tripalmitine) optionally in admixture with a biodegradable polymer. Examples of suitable microcapsules and of the preparation thereof are disclosed, for instance in Ref. 8 and Ref. 9, herein incorporated by reference in their entirety. Microcapsules having a proteinaceous envelope, i.e. made of natural proteins (albumin, haemoglobin) such as those described in Ref. 44 or Ref. 45 (here incorporated by reference), can also be employed. Also in this case, the polymer (e.g. PEG or mPEG) liable of being recognised by the APA, is preferably bound to a compound compatible with the components forming the respective envelope of the microcapsules, e.g. a polymer (e.g. polymethacrylate, polystyrene or poly(L-lactide)), an amphiphilic lipid as illustrated above or a protein (e.g. albumin or lactalbumin), in the same molar amounts as previously illustrated. Any biocompatible gas, gas precursor or mixture thereof may be employed to fill the above microvesicles (hereinafter also identified as "microvesicle-forming gas").

The gas may comprise, for example, air; nitrogen; oxygen; carbon dioxide; hydrogen; nitrous oxide; a noble or inert gas such as helium, argon, xenon or krypton; a radioactive gas such as $Xe^{133}$ or $Kr^{81}$; a hyperpolarized noble gas such as hyperpolarized helium, hyperpolarized xenon or hyperpolarized neon; a low molecular weight hydrocarbon (e.g. containing up to 7 carbon atoms), for example an alkane such as methane, ethane, propane, butane, isobutane, pentane or isopentane, a cycloalkane such as cyclobutane or cyclopentane, an alkene such as propene, butene or isobutene, or an alkyne such as acetylene; an ether; a ketone; an ester; halogenated gases, preferably fluorinated gases, such as or halogenated, fluorinated or perfluorinated low molecular weight hydrocarbons (e.g. containing up to 7 carbon atoms); or a mixture of any of the foregoing. Where a halogenated hydrocarbon is used, preferably at least some, more preferably all, of the halogen atoms in said compound are fluorine atoms.

Fluorinated gases are preferred, in particular perfluorinated gases, especially in the field of ultrasound imaging. Fluorinated gases include materials which contain at least one fluorine atom such as, for instance fluorinated hydrocarbons (organic compounds containing one or more carbon atoms and fluorine); sulfur hexafluoride; fluorinated, preferably perfluorinated, ketones such as perfluoroacetone; and fluorinated, preferably perfluorinated, ethers such as perfluorodiethyl ether. Preferred compounds are perfluorinated gases, such as $SF_6$ or perfluorocarbons (perfluorinated hydrocarbons), i.e. hydrocarbons where all the hydrogen atoms are replaced by fluorine atoms, which are known to form particularly stable microbubble suspensions, as disclosed, for instance, in Ref. 4.

The term perfluorocarbon includes saturated, unsaturated, and cyclic perfluorocarbons. Examples of biocompatible, physiologically acceptable perfluorocarbons are: perfluoroalkanes, such as perfluoromethane, perfluoroethane, perfluoropropanes, perfluorobutanes (e.g. perfluoro-n-butane, optionally in admixture with other isomers such as perfluoroisobutane), perfluoropentanes, perfluorohexanes or perfluoroheptanes; perfluoroalkenes, such as perfluoropropene, perfluorobutenes (e.g. perfluorobut-2ene) or perfluorobutadiene; perfluoroalkynes (e.g. perfluorobut-2-yne); and perfluorocycloalkanes (e.g. perfluorocyclobutane, perfluoromethylcyclobutane, perfluorodimethylcyclobutanes, perfluorotrimethylcyclobutanes, perfluorocyclopentane, perfluoromethylcyclopentane, perfluorodimethylcyclopentanes, perfluorocyclohexane, perfluoromethylcyclohexane and perfluorocycloheptane). Preferred saturated perfluorocarbons include, for example, $CF_4$, $C_2F_6$, $C_3F_8$, $C_4F_8$, $C_4F_{10}$, $C_5F_{12}$ and $C_6F_{14}$.

It may also be advantageous to use a mixture of any of the above gases in any ratio. For instance, the mixture may comprise a conventional gas, such as nitrogen, air or carbon dioxide and a gas forming a stable microbubble suspension, such as sulfur hexafluoride or a perfluorocarbon as indicated above. Examples of suitable gas mixtures can be found, for instance, in Ref. 46, which is herein incorporated by reference. The following combinations are particularly preferred: a mixture of gases (A) and (B) in which the gas (B) is a fluorinated gas, selected among those previously illustrated, including mixtures thereof, and (A) is selected from air, oxygen, nitrogen, carbon dioxide or mixtures thereof. The amount of gas (B) can represent from about 0.5% to about 95% v/v of the total mixture, preferably from about 5% to 80%.

Particularly preferred gases are $SF_6$, $C_3F_8$, $C_4F_{10}$ or mixtures thereof, optionally in admixture with air, oxygen, nitrogen, carbon dioxide or mixtures thereof.

In certain circumstances it may be desirable to include a precursor to a gaseous substance (i.e. a material that is capable of being converted to a gas in vivo). Preferably the gaseous precursor and the gas derived therefrom are physiologically acceptable. The gaseous precursor may be pH-activated, photo-activated, temperature activated, etc. For example, certain perfluorocarbons may be used as temperature activated gaseous precursors. These perfluorocarbons, such as perfluoropentane or perfluorohexane, have a liquid/gas phase transition temperature above room temperature (or the temperature at which the agents are produced and/or stored) but below body temperature; thus, they undergo a liquid/gas phase transition and are converted to a gas within the human body.

For the use in MRI the microvesicles will preferably contain a hyperpolarized noble gas such as hyperpolarized neon, hyperpolarized helium, hyperpolarized xenon, or mixtures thereof, optionally in admixture with air, carbon dioxide, oxygen, nitrogen, helium, xenon, or any of the halogenated hydrocarbons as defined above.

For use in scintigraphy, the microvesicle will preferably contain radioactive gases such as $Xe^{133}$ or $Kr^{81}$ or mixtures thereof, optionally in admixture with air, carbon dioxide, oxygen, nitrogen, helium, krypton or any of the halogenated hydrocarbons as defined above.

In addition to their use as diagnostic agents, gas-filled microvesicles can also be used for delivering a therapeutic agent, as illustrated for instance in Ref. 47, Ref. 48 or Ref. 49, all herein incorporated by reference. Typically, the gas-filled microvesicles are administered with the desired therapeutic agent (either in admixture therewith or associated thereto) and, once the microvesicles and therapeutic agent reach the desired region of interest in the patient, the application of a controlled acoustic power capable of destroying the gas-filled microvesicles will produce an (ultrasound-mediated) release of the therapeutic agent in said region.

Liposomes

Liposomes can advantageously be used as carriers for any of the previously mentioned contrast agents, in particular MRI or X-ray contrast agents, or for the above illustrated therapeutic agents.

Preferred materials for preparing liposomes are phospholipids, such as those previously listed, optionally in admixture with other amphiphilic compounds, such as those previously listed. Liposomes for use in the invention further contain a hydrophilic polymer, such as those previously listed, particularly preferred being PEG or mPEG, advantageously inserted into the liposome structure by covalently binding the polymer to a compound comprised in the stabilizing envelope, particularly a phospholipid. Preferred molar amounts of hydrophilic polymer are as previously illustrated in connection with the formulation of gas-filled microvesicles.

For preparing liposome suspensions, conventional techniques known in the art can be used. Said preparation techniques typically involve dissolving the compounds forming the liposome (e.g. phospholipids) in an organic solvent, evaporating the organic solvent under vacuum to obtain a film of the liposome-forming compounds and finally hydrating said film. Typically, when the liposome-forming compound is a phospholipid, the hydration is performed at a temperature above phospholipid transition temperature. Preferably, the so obtained liposomes are subsequently calibrated at the desired size by narrowing the vesicles size distribution within appropriate limits, e.g. by extrusion through conveniently graded filtration membranes. For encapsulating a desired contrast or therapeutic agent ("active compound") in the internal portion of the liposome, e.g. as an aqueous solution or suspension of said active compound, a preferred method involves using a solution or suspension of said active compound to hydrate the lipids at or above the lipid transition temperature, with subsequent washing (e.g. by dialysis) of the obtained liposomes, to remove the excess of non-encapsulated solution or suspension. Alternatively, the lipids are first hydrated in an unloaded aqueous carrier, and then the active compound is introduced in the interior of the liposome by transmembrane permeation loading, by incubation of the obtained liposomes in the presence of a concentrated solution of the active compound (see e.g. Ref. 50 herein incorporated by reference), with subsequent washing of the liposomes.

The desired size reduction of liposomes is obtained according to conventional techniques, including sonication, extrusion or microfluidisation of the initial liposome suspension. Accordingly, hydrated liposomes obtained as above described may be exposed to ultrasonic radiations to suitably reduce the liposome dimensions. Alternatively, the hydrated liposomes can be extruded through a plurality of membranes (e.g. of polycarbonate) with decreasing pore size (e.g. 2.0, 1.0, 0.8, 0.6, 0.4, and 0.2 µm), to reduce the liposome size to the final desired dimension. As a further alternative, large vesicles can be homogenised under high pressure in a microfluidizer (e.g. from Microfluidics Corporation), to progressively reduce the liposome size to the desired size, depending on the amount of recirculation of the liposomes in the microfluidizer.

Preferably, after size reduction, about 80% of the vesicles are ±10% from any nominal value selected between 0.2 to 1.0 µm. Any other broader or narrower distribution within the foregoing limits is however admissible. After size-reduction treatment, the suspension is preferably checked to ensure that the concentration of lipids in the liposome suspension is adequate, this being optionally adjusted to be in conformity with the desired application. Adjustment can be effected by dilution with a larger volume of carrier liquid, if the lipid concentration exceeds the desired limits; on the other hand, the concentration can be increased by usual means, for instance by micro- or ultra-filtration on membranes of appropriate porosity which retain the vesicles but which are permeable to the carrier liquid. The insertion of the polymer liable of being recognised by the APA, is preferably made by binding it to a compound compatible with the components forming the envelope of the liposome, preferably an amphiphilic lipid compound (e.g. a phospholipid), as explained above.

A review of liposomes and their preparation methods can also be found in reference books, such as Ref. 51.

The desired contrast agent (preferably an MRI responsive agent) or therapeutic agent can be inserted into the liposome structure, either by enclosing the compound in the interior of the liposome or by binding it to the liposome's membrane (the phospholipid bilayer) or to the surface of the liposomes. For instance, magnetite nanoparticles or a therapeutic agent can be suspended in the liquid interior of the liposome the liposome. Alternatively, chelated paramagnetic ions can be bound to a compound compatible with the components forming the envelope of the liposome, preferably an amphiphilic lipid compound (e.g. a phospholipid), as explained above. According to a preferred embodiment (as disclosed e.g. in Ref. 52, herein incorporated by reference) micelles containing the MRI contrast agent can be associated (e.g. by electrostatic interaction), with the surface of the liposome. Advantageously, use of liposomes allows relatively high loads of therapeutics and/or diagnostic agents in the structure thereof.

Preferred paramagnetic metal ions have atomic numbers 21-29, 42, 44, or 57-83, including ions of the transition metal or lanthanide series which have at least one, and more preferably five or more, unpaired electrons and a magnetic moment of at least 1.7 Bohr magneton. Preferred paramagnetic metals include, but are not limited to, chromium (III), manganese (II), manganese (III), iron (II), iron (III), cobalt (II), nickel (II), copper (II), praseodymium (III), neodymium (III), samarium (III), gadolinium (III), terbium (III), dysprosium (III), holmium (III), erbium (III), europium (III) and ytterbium (III). Preferred paramagnetic ion is Gadolinium. The paramagnetic ion is preferably chelated with a chelating moiety or chelator. Suitable chelators known in the art include acids with methylene phosphonic acid groups, methylene carbohydroxamine acid groups, carboxyethylidene groups, or carboxymethylene groups such as, for instance, diethylenetriamine pentaacetic acid (DTPA), 1,4,7,10-tetraazacyclododecane-1,4,7,10-tetraacetic acid (DOTA), 1,4,7,-tricarboxymethyl 1,4,7,10 teraazacyclododecane triacetic acid (DO3A), such as 1,4,7,10-tetraazacyclo-dodecan-1-(2-hydroxypropyl)-4,7,10-triacetic acid (HP-DO3A), ethylenediaminetetraacetic acid (EDTA), and 1,4,8,11-tetraazacyclotetradecane-1,4,8,11-tetraacetic acid (TETA). Any of these chelated paramagnetic ions can be bound to a suitable amphiphilic lipid (e.g. phosphatidylethanolamine) as illustrated above and the obtained construct admixed with the other components of the liposomal envelope, according to known techniques.

Examples of further contrast agents which may be incorporated in liposomes include, for instance, iodinated compounds, such as iomeprol or iopamidol (commercially available from Bracco Imaging); compounds comprising a hyperpolarized atom, such as $^{13}C$, $^{15}N$, $^{19}F$, $^{23}Na$, $^{31}P$ or $^{35.5}Cl$, including for instance [$^{13}C$]urea (see e.g. Ref. 54) or bis-1,1-hydroxymethyl-1-$^{13}C$-cyclopropane-$D_8$ (see e.g. Ref. 55); radiopharmaceutical agents, such as for instance complexes of Technetium ($^{99m}Tc$), Gallium ($^{67}Ga$ or $^{68}Ga$), Indium ($^{111}In$) or Thallium ($^{201}Tl$); or optical or nuclear imaging agent as defined above.

Liposomes/Microvesicles and Targeting Construct

The targeting construct can be associated with the liposome or gas-filled microvesicle in many different manners and at many different steps of the contrast/therapeutic methodology.

According to an embodiment, the targeting construct can be admixed with the components forming the supramolecular assembly at any suitable stage of any preparation procedures illustrated above. For instance, in the case of the process disclosed in Ref. 7, the targeting construct can be admixed with the components of the initial mixture, undergoing to the emulsion and lyophilisation steps. Alternatively, a suspension containing the construct can be separately prepared and subsequently added to the already formed emulsion (containing the other film-forming components), preferably under heating. Alternatively, the targeting construct can be admixed (e.g. as a suspension) with a suspension of the supramolecular assembly, and the resulting mixture containing the targeting construct bound to the assembly can be either used as such for administration or can undergo a further lyophilisation step before final reconstitution and use.

According to preferred embodiments, the targeting construct is administered separately to the patient, before the administration of the contrast agent (e.g. gas-filled microvesicles). After a predetermined period of time (e.g. to allow effective accumulation of the targeting construct in a desired region of interest), the contrast agent will then be administered. The contrast agent will thus associate with the targeting construct inside the body of the patient, particularly in the region of interest where the targeting ligand of the construct will be bound to a corresponding target site.

Pharmaceutical Kit, Administration and Imaging

A pharmaceutical kit comprising liposomes or gas-filled microvesicles and a targeting construct according to the invention may be presented in different forms, depending on the manner the liposomes or microvesicles are associated with the targeting construct.

According to a preferred embodiment, the pharmaceutical kit contains at least two components, the first one being liposomes or gas-filled microvesicles (or a precursor thereof) and the second one being a targeting construct. Optionally, one or more further different targeting construct (e.g. with the same anti-polymer antibody but different targeting ligand) may be included in the kit. Typically, each component is contained in a respective separate container. Alternatively, a mixture of different targeting constructs may be contained in a single container.

Preferably, the first container comprises a precursor of gas-filled microvesicles in powdered dry form, in contact with a microvesicle-forming gas.

The second component can be present in the container in dry solid form or as a suspension in a physiologically acceptable aqueous carrier.

The above kit can optionally contain a physiologically acceptable aqueous carrier (either in a separate container or in a dual chamber container), for reconstitution of the dry components before injection.

The reconstitution of the components will depend upon the chosen methodology of administration. For instance, if the targeting construct and the contrast/therapeutic agent are administered separately, the two components will accordingly be reconstituted separately with the respective carrier. Alternatively, if it is foreseen to assemble the liposomes or gas-filled microvesicles with the targeting construct in advance, for the concurrent administration thereof, the two compositions may be sequentially reconstituted with the same carrier.

Alternatively, when a lyophilized composition contains a microvesicle's precursor already admixed with a targeting construct, the kit may comprise a first container, containing the lyophilized composition in contact with a selected microvesicle-forming gas (as those previously discussed) and a second container, containing a physiologically acceptable aqueous carrier.

The assembly of the present invention may be used in a variety of in-vivo and in-vitro contrast imaging methods, including in particular ultrasound imaging. Contrast imaging includes any contrast enhanced imaging of a body part or tissue, as well as any other diagnostic technique or method such as, for instance, quantification diagnostic techniques (including e.g. blood pressure, flow and/or perfusion assessment).

Typically, a patient is administered an effective amount of the assembly (e.g. by injection), either as separate components or as a an already formed assembly, and the body part or tissue to be imaged or treated ("region of interest") is subjected to the desired imaging methodology. The term patient includes any subject (human or animal) undergoing to the administration of the assembly, either for diagnostic/therapeutic purposes or for experimental purposes (including, for instance, use of a contrast agent in laboratory animals, e.g. to follow an experimental therapeutic treatment).

According to a preferred embodiment, schematically illustrated in FIG. 4, an effective amount of a targeting construct (in a concentration of e.g. from about 1 nmoles/kg to 500 nmoles/kg, preferably 5 nmoles/kg to 50 nmoles/kg, more preferably 10 nmoles/kg to 30 nmoles/kg, depending e.g. from the type of construct and/or the type of targeting ligand) is first administered to a patient, typically by injection of a suspension thereof. The composition is then allowed to circulate in the vascular system of the patient for a time sufficient for the targeting construct 401 to reach the region of interest 404 (i.e. the region which is supposed to express or contain the respective target or receptor 405 for the targeting ligand 403 of the construct), and binding thereto through the respective targeting ligand 403, as illustrated in FIG. 4a. For the sake of clarity, the bi-specific targeting construct 401 has been indicated in FIG. 4 as comprising only one targeting ligand 403 and one anti-polymer antibody 402, but it is understood that this schematization includes any of the previously illustrated targeting constructs. Afterwards, a suspension of the desired contrast/therapeutic agent 406 (e.g. gas-filled microvesicles in this case) containing the hydrophilic polymer 407 is injected into the patient and the region of interest is imaged with a suitable imaging technique and/or subjected to the desired therapeutic treatment (e.g. ultrasound mediated release of therapeutic agent). The time interval between the administration of the targeting construct and the administration of the contrast agent can be easily determined by the practitioner based on common medical practice, depending, for instance, on the patient (e.g. type, age, weight), the type and properties of the targeting construct (e.g. its half-life in blood and/or its accumulation in the target tissue/region) the type of imaging method and/or treatment and on the location of the region of interest. For instance, in the case of ultrasound imaging with gas-filled microvesicles, the time interval between the two administrations may vary, for instance, from about 5 minutes to about 48 hours, typically from about 30 minutes to about 24 hours. The imaging of the region of interest will thus be enhanced by the presence of the microvesicles 406 bound, through the final portion 408 of polymer 407 contained in the envelope thereof, to one or more anti-polymer antibody 402 of the targeting construct 401 immobilized in the region of interest 404, as illustrated in FIG. 4b.

A variety of imaging techniques may be employed in ultrasound applications, for example including fundamental and harmonic B-mode imaging, pulse or phase inversion imaging and fundamental and harmonic Doppler imaging; if desired three-dimensional imaging techniques may be used. Furthermore, diagnostic techniques entailing the destruction of gas-filled microvesicles (e.g. by means of ultrasound waves at high acoustical pressure) are also contemplated, for instance in methods for assessing blood perfusion.

Microvesicles according to the invention can typically be administered in a concentration of from about 0.01 to about 5.0 µl of gas per kg of patient, depending e.g. on their respective composition, the tissue or organ to be imaged and/or the chosen imaging technique. This general concentration range can of course vary depending from specific imaging applications, e.g. when signals can be observed at very low doses such as in color Doppler or power pulse inversion. Possible other diagnostic imaging applications include scintigraphy, light imaging, and X-ray imaging, including X-ray phase contrast imaging.

The following non-limitative examples are intended better illustrate the invention. Examples 1-9, 11 and 14-21 are actual examples, while examples 10, 12, 13 and 22-30 are prophetic examples

EXAMPLES

The following abbreviations and materials are employed in the subsequent examples:

| | | |
|---|---|---|
| PEG4000 | Polyethylenglycol, MW = 4000 | Fluka |
| DMF | Dimethlyformamide | Fluka |
| cysteine | | Sigma |
| DPPE-mPEG5000 | 1,2-dipalmitoyl-sn-glycero-3-phosphoethanolamine-N-methoxypolyethyleneglycol 5000 | Genzyme |
| DSPE-mPEG2000 | 1,2-dipalmitoyl-sn-glycero-3-phosphoethanolamine-N-methoxypolyethyleneglycol 2000 | Genzyme |
| DSPC | 1,2-distearoyl-sn-glycero-3-phospholcholine | Genzyme |
| Palmitic acid | | Fluka |
| DSPE-PEG2000-maleimide | 1,2-distearoyl-sn-glycero-3-phosphoethanolamine-N-[maleimide(polyethylene glycol 2000)] | Avanti Polar |
| TCEP | tris(2-carboxyethyl)phosphine | Pierce |
| Tris HCl | 2-Amino-2-(hydroxymethyl)-1,3-propanediol, hydrochloride | |
| EDTA | Ethylenedinitrilotetraacetic acid | Fluka |
| Phosphate buffered saline (PBS) | 10 mM phosphate, 150 mM sodium chloride, pH7.4 | Sigma |
| DPPG.Na | 1,2-dipalmitoyl sn-glycero-[3-phospho-rac-(1-glycerol)] sodium saltglycerol | Genzyme |
| DIO | 3,3'-dioctadecyloxacarbocyanineperchlorate | Invitrogen |
| Tween ® 20 | Polysorbate 20 | Sigma |
| Lactel ® | mPEG-co-poly(lactic-co-glycolic) acid | Adsorbable polymers |

Example 1

Preparation of Biotinylated Anti-Mouse P-Selectin Antibody 1 mg of Chromalink biotin 354S (ref. #B-1001-110, Solulink, USA) was dissolved in DMF (100 µL) at room temperature, yielding a 12.3 mM solution. The solution (10 mol equiv.) was added to a solution of a rat anti mouse P-Selectin antibody (clone RB40.34, ref. #553741, BD Biosciences, USA), prepared by dissolving 1 mg/mL of antibody in phosphate buffer saline (pH 7.4). The reaction mixture was allowed to incubate at room temperature for 2 hours and then purified by gel filtration with Zeba spin columns, equilibrated in PBS (2 min 1,000 g, Pierce, USA). The obtained biotinylated antibody contained 2.0 biotin residues per antibody's molecule as determined by spectrometric measurement following manufacturer recommendations.

Example 2

Preparation of Biotinylated Anti-mPEG Antibody

Example 1 was repeated by replacing the anti-mouse P-Selectin antibody with rabbit anti-mPEG antibody (clone PEG- B-47, ref. 2061-1, from Epitomics, USA). The obtained biotinylated antibody contained 1.9 biotin residues per antibody's molecule.

Example 3 (Comparative)

Preparation of Biotinylated of Rat Isotype Antibody (Control)

Example 1 was repeated by replacing the anti-mouse P-Selectin antibody with a rat isotype control antibody (Affinity purified rat IgG1 isotype control, eBioscience, ref #14-4301). The obtained biotinylated antibody contains 1.9 biotin residues/antibody molecule.

Example 4

Preparation of Bi-Specific Targeted Streptavidin (Anti Mouse P-Selectin Antibody and Anti mPEG Antibody)

10 μg of biotin-anti mouse P-Selectin antibody, prepared according to example 1, and 10 μg of biotin-anti mPEG antibody, prepared according to example 2, were dissolved into 800 μL of phosphate buffer saline pH 7.4. Then, the antibody mixture was added under agitation to 28.3 μL of a solution of streptavidin (1 mg/mL), prepared by dissolving streptavidin (IBA, ref. #2-0203-100) in distilled water. The solution was mixed at 25° C. for 30 minutes.

Example 5 (Comparative)

Preparation of Bi-Specific Control Streptavidin (Control)

Example 4 was repeated by replacing the biotin-anti mouse P-Selectin antibody with the biotin rat isotype control antibody prepared according to example 3.

Example 6

Preparation of mPEG-Containing Gas-Filled Microvesicles 27 mg of DSPC and 2.2 mg of palmitic acid were dissolved in 3.9 g of cyclooctane at 60° C. The obtained solution was cooled to room temperature and dispersed in 50 mL of distilled water containing 5.5 g of PEG4000 (Fluka) and 19 mg of DPPE-mPEG5000 by using a high speed homogenizer (Polytron T3000) for 1 minute at 8000 rpm. The resulting emulsion was heated under stirring at 80° C. for 1 hour, and then cooled to room temperature. The resulting emulsion was diluted 5 times in distilled water containing 10% of PEG4000 then filled in DINER vials (0.75 mL per vial). The vials were frozen at −50° C. for 2 hours (Christ Epsilon lyophilizer), then freeze-dried at −20° C. and 0.5 mBar for 12 hours, with a final drying step at 30° C. and 0.2 mBar for 6 hours.

The lyophilized product was then exposed to an atmosphere containing 35% of perfluoro-n-butane and 65% of nitrogen and the vials were sealed.

The title mPEG-containing gas-filled microvesicles were finally obtained by reconstitution of the vial (lyophilized cake+gas) with 2 mL of saline solution (0.9% NaCl) by gentle hand shaking.

Example 7

In Vitro 2-Step Binding with Bi-Specific Streptavidin (Anti Mouse P-Selectin Antibody and Anti-mPEG Antibody) and mPEG-Containing Gas-Filled Microvesicles a. Preparation of Glass Coverslip Coated with Mouse Fc-P-Selectin Briefly, dry powder of mouse Fc P-Selectin (50 μg, R&D System, ref. #737-PS-050) is dissolved in 100 μL pf PBS pH 7.4 in a glass vial, then transferred in 12.4 mL of PBS to yield a 4 μg/mL solution of mouse Fc P-Selectin. The solution of mouse Fc P-Selectin (400 μL of 4 μg/mL) is deposited on 40 mm glass coverslips and incubated overnight at 4° C. Then, the excess of mouse Fc P-Selectin solution is discarded and replaced by a blocking solution (500 μL of PBS containing 1% (w/v) of BSA) for 2 hours at room temperature. The coverslips are washed with a washing solution (3 mL of PBS containing 0.05% Tween) and then stored at −20° C. Prior to use, the mouse Fc P-Selectin coated coverslips are allowed to equilibrate at room temperature.

b. Binding Test

The glass coverslip prepared as above described was incubated for 30 minutes with 400 μL of the bi-specific streptavidin suspension prepared according to example 4. Then, the coverslip was mounted in a flow chamber (FCS2, Bioptech, USA). The mPEG-containing gas-filled microvesicles prepared according to example 6 were drawn through the flow chamber, and their adhesion onto the coating layer of the coverslip was assessed for 10 min at a flow rate of 1.0 mL/min (shear rate of 114 $s^{-1}$) in the presence of 50% human plasma in PBS (v:v, Biomeda collected on citrate, ref. ES1020P, Stehelin & Cie AG). A quantitative analysis of microvesicles accumulation was performed by counting the number of microvesicles adhering in the observed area at 2 min intervals over the total 10 min infusion, using the image processing program Analysis FIVE (SIS, Germany). After 10 min, five pictures were taken randomly and averaged then divided by ten, the obtained number representing the rate of microvesicles accumulation per minute (RMA/min). Each observed area was 183×137 μm, as measured with the aid of a stage micrometer. Imaging was performed between the middle and the exit of the chamber. A mean value of 4.5 RMA/min was determined, indicating a good binding of the micovesicles to the anti mPEG antibody of the bi-specific targeted streptavidin, in turn attached to the surface of the coated coverslip through the anti mouse P-Selectin antibody.

Example 8 (Comparative)

In Vitro 2-Step Binding with Bi-Specific Streptavidin (Isotype Control Antibody and Anti-mPEG Antibody) and mPEG Containing Gas Microvesicles Example 7 was repeated, by incubating for 30 minutes glass coverslip coated with mouse Fc P-Selectin with 400 μL of the non-binding bi-specific streptavidin prepared according to comparative example 5. A mean value of 0.02 RMA/min was determined, indicating that substantially no binding of microvesicles to the surface of the coverslip.

Example 9

Preparation of Thiolated CD62P Antibody

A solution of purified anti P-selectin antibody clone RB40.34 was reacted with 20 μL of a 10 mM Sulfo-LC-SPDP solution ((Sulfosuccinimidyl 6-[3'-(2-pyridyldithio)propionamido]-hexanoate), Pierce, #21650) in 80 µL of 50 mM phosphate buffer 150 mM NaCl pH 7.4, for 40 min at room temperature. The solution was spun through a 2 mL spin-column at 1000 g (Zeba spin column, Pierce, #89889) equilibrated in phosphate buffer 5 mM pH7.4. The functionalized antibody was then reduced with 1 mM TCEP, 50 mM Tris HCl/5 mM EDTA pH 6.8, for 10 min at room temperature. The reduced antibody was then spun through a 2 mL spin-column at 1000 g, to obtain a suspension of thiolated antibody.

Example 10

Preparation of Thiolated Anti-PEG Antibody

Example 9 is repeated, by replacing the anti-mouse monoclonal antibody with anti-mPEG Rabbit Monoclonal Antibody (from Epitomics #2061-1), to obtain a solution of anti-mPEG antibody.

Example 11

Preparation of Maleimide-Functionalized Micelles 2 mg (0.69 µmoles) of DSPE-PEG2000-maleimide were dissolved in ethanol at 40° C. The solvent was removed under $N_2$ at 40° C. to obtain a lipid film. The lipid film was dried under vacuum (0.2 mBar) at 25° C. overnight. The dried film was hydrated in 0.5 mL of phosphate buffer (50 mM pH=6.5) at 60° C. to obtain a clear suspension of DSPE-PEG2000-maleimide micelles.

Example 12

Preparation of Bi-Specific Targeted Micelles

325 µL of the suspension of thiolated anti P-selectin antibody clone RB40.34 prepared according to Example 9 and 325 µL of the suspension of the thiolated anti-mPEG antibody prepared according Example 10 are mixed and added to 250 µL of micellar suspension prepared according to Example 11. The mixture is mixed at 25° C. for 3 hours. Then cysteine (0.69 µmole) is added to the solution to block the remaining maleimide groups. The obtained bi-specific targeted micelles are used without further purification.

Example 13

Preparation of Covalently Conjugated Bi-Specific Antibodies

Rabbit monoclonal IgG anti-mPEG (clone PEG-B-47, Epitomix, USA) and anti P-selectin antibody clone RB40.34 are diluted down to 1.5 mg/mL (i.e. 10 µM) in modification buffer (100 mM phosphate, 150 mM sodium chloride, pH 7.2-BupH™ PBS, Pierce, Switzerland).
Succinimidyl 4-hydrazinonicotinate acetone hydrazone (SANH, Pierce, Switzerland) is diluted down to 2.9 mg/mL in DMSO (10 mM). Succinimidyl 4-formylbenzoate (SFB, Pierce, Switzerland) is diluted down to 2.47 mg/mL in DMSO (i.e. 10 mM).
One of the antibodies (100 µg) is reacted for 1 hour at room temperature with diluted SANH to achieve a 5 fold molar excess of modification reagent. The same amount of the other antibody is reacted for 1 hour at room temperature with diluted SFB to achieve a 5-20 fold molar excess of modification reagent. Both antibodies are dialysed against conjugation buffer (100 mM MES, 150 mM NaCl pH 4.7-BupH™ MES, Pierce, Switzerland) then mixed together and incubated for 2 hours at room temperature.
Heterodimer conjugates are isolated by size exclusion chromatography on a Sephacryl® S300 column.

Example 14

Preparation of Bi-Specific Targeted Liposomes 30.2 mg of cholesterol, 73.2 mg of DSPC, 23.0 mg of DPPG.Na and 3.6 mg of DIO were dissolved in 20 mL of chloroform at 65° C. followed by addition of 31 µL of 3H cholesteryl hexadecyl ether. The solvent was evaporated and the mixture of components dried for 2 hours under vacuum. The residue was resuspended in a distilled water, up to a concentration of 10 mg/mL, to obtain a suspension of liposomes. The suspension was subsequently extruded on filters of 1 um, 0.6 um and 0.4 um, to reduce the size of the liposomes. The liposome suspension was dialysed against a phosphate buffered glucose solution. Then 10.5 mg of DSPE-PEG2000-maleimide were dissolved in 0.5 mL of phosphate buffered glucose solution. This solution was added to the liposome suspension. The suspension was maintained at 65° for 1 hour, to allow insertion of the maleimide derivative in the structure of the liposomes. Then 472 µL of a 10 mg/mL solution of streptavidin were processed according to the procedure described in example 9, to obtain a corresponding thiolated streptavidin. The thiolated streptavidin was added to the liposome suspension and reacted for 2.5 hours at room temperature. The liposome suspension was purified by centrifugation (30 min at 30000 g) and then resuspended in Tris buffered glucose solution.
Subsequently, 65.5 pmol of rat IgG1 anti-mouse CD62P (prepared as described in example 1) and 65.5 pmol of rabbit anti-PEG antibody (prepared as described in example 2) were mixed in 1090 µL of PBS. The mixture was then added to 19 µL of the liposome suspension prepared above, to obtain the desired bi-specific liposomes.

Example 15

Preparation of Comparative (not Anti-PEG Binding) Targeted Liposomes

A liposome suspension was prepared as described in example 14, with the difference that the rabbit anti-PEG antibody has been replaced by biotinylated rabbit non specific IgG.

Example 16

Preparation of Comparative (not Anti-P-Selectin Specific) Targeted Liposomes

A liposome suspension was prepared as described in example 14, with the difference that the anti P-selectin antibody clone RB40.34 has been replaced by a rat non-specific IgG1.

Example 17

In Vitro 2-Step Binding with Bi-Specific Liposomes (Anti P-Selectin Antibody and Anti-mPEG Antibody) and mPEG-Containing Gas-Filled Microvesicles Thermanox® disks were coated with mouse-Fc-P-selectin according to the methodology described in example 7. The coated disks were placed in wells of a 24-well plate.

Then, the liposome suspension prepared according to example 14 was incubated over the Thermanox disks for 4 hours (500 μL in each well).

The disks were then washed (five times) with PBS (1 mL for each well and each washing), to remove unbound liposomes.

Then, 600 μl of a suspension of microbubbles prepared according to example 6 were added to each well. After 1 hour, the disks were washed twice with PBS and analysed by light microscopy (Leica DC300S DMR, with Q-Win image analysis software), to determine the mean percentage of effectively covered by microbubbles.

A mean surface coverage of 60.8% was determined.

The procedure was repeated by replacing the liposome preparation of example 14 with comparative preparations of examples 15 and 16, respectively. The observed mean surface coverage was of 0.8% and of 1.3%, respectively.

Example 18

Preparation of mPEG-Containing Liposomes 30.2 mg of cholesterol, 73.2 mg of DSPC, 23.0 mg of DPPG.Na and 3.6 mg of DIO were dissolved in 20 mL of chloroform at 65° C. followed by addition of 31 μL of radioactive marker 3H cholesteryl hexadecyl ether. The solvent was evaporated and the mixture of components dried for 2 hours under vacuum. The residue was resuspended in a distilled water, up to a concentration of 10 mg/mL, to obtain a suspension of liposomes. The suspension was subsequently extruded on filters of 1 um, 0.6 um and 0.4 um. The liposome suspension was dialysed against a phosphate buffered glucose solution. Then 10.5 mg of DSPE-mPEG2000 were dissolved in 0.5 mL of phosphate buffered glucose solution. This solution was added to the liposome suspension. The suspension was maintained at 65° for 1 hour, to allow insertion of the maleimide derivative in the structure of the liposomes. The liposome suspension was purified by centrifugation (30 min at 30000 g) and then resuspended in Tris buffered glucose solution.

Example 19

In Vitro 2-Step Binding with Bi-Specific Streptavidin (Anti Mouse P-Selectin Antibody and Anti-mPEG Antibody) and mPEG-Containing Liposomes (19a)

Thermanox® disks were coated with mouse-Fc-P-selectin according to the methodology described in example 7. The coated disks were placed in wells of a 24-well plate. Then, the bi-specific streptavidin solution prepared according to example 4 was incubated over the Thermanox disks for 1 hour (400 μL in each wells).

The disks were then washed (three times) with PBS (1 mL for each well and each washing), to remove unbound bi-specific streptavidin.

Then, a 400 μL of a suspension of liposomes prepared according to example 18 were added to each well. After 4 hours, the disks were washed four fold with PBS and analysed by radioactivity counting (expressed as dpm: disintegrations per minute) by using a liquid scintillation analyzer (2200CA-Tri-Carb, Packard) to determine the amount of bound liposomes.

Similar experiment was repeated with bi-specific streptavidin solution prepared according to example 5 (19b).

A third experiment (19c) was repeated with bi-specific streptavidin solution prepared according to example 4, but with a biotin rat isotype control antibody instead of biotin-anti mPEG antibody.

The results are illustrated in the following table, showing that comparative experiments provide substantially no liposome binding to the disks.

| Example | bi-specific streptavidin | dpm |
|---------|--------------------------|-----|
| 19a | Anti P-selectin/anti-mPEG | 227 |
| 19b | Control/anti-mPEG | 34 |
| 19c | Anti P-selectin/control | 22 |

Example 20

Preparation of Iomeprol-Loaded Pegylated Liposomes 70.3 mg of DSPC, 22.1 mg of DPPG.Na and 29.1 mg of cholesterol were dissolved in 20 mL of chloroform. The solution was heated to 60° C. in a round-bottom flask, chloroform was evaporated under reduced pressure and the residual solvent was completely removed under maximal vacuum in a vacuum oven for 3 hours. Then, the lipids were re-hydrated with a solution of iomeprol (Bracco Imaging) containing 775 mg of iomeprol/mL to form iomeprol-loaded liposomes. The suspension of liposomes was then extruded through filters with selected pore sizes, down to 0.2 μm. The obtained calibrated liposomes were then dialysed against a solution of glucose 5%. A solution of DSPE-PEG2000 was dissolved in Tween 20 mM at pH of 7.4 and 1 mL of this solution was added to 10 mL of the suspension of liposomes. This mixture was shaken and incubated at 65° C. for 1 hour. The iomeprol-loaded pegylated liposomes were obtained and ready for further use as X-ray contrast agent.

Example 21

Preparation of Bi-Specific Targeted Streptavidin (Mouse Anti Human Fibrin Antibody and Anti mPEG Antibody)

Example 1 is repeated, by replacing the anti P-selectin antibody clone RB40.34 with a biotin-mouse anti human fibrin antibody. 10 μg of the fibrin antibody and 10 μg of biotin-anti mPEG antibody (prepared according to example 2) are dissolved into 800 μL of phosphate buffer saline pH 7.4. Then, the antibody mixture is added under agitation to 28.3 μL of a solution of streptavidin (1 mg/mL), prepared by dissolving streptavidin (IBA, ref. #2-0203-100) in distilled water and the solution is mixed at 25° C. for 30 minutes.

Example 22

In Vivo Targeted Administration of Iomeprol Loaded Liposomes

A human blood clot is inserted in the left carotid artery of a rat. Then, bi-specific constructs prepared according to example 21 are injected intravenously to the rat. Two hours later, iomeprol containing liposomes prepared according to example 21 are injected intravenously to the rat, at an iomeprol dose of 0.5 mg/kg. Then, imaging of contrast enhanced thrombus is achieved by means of computed tomography in the rat. Contrast of thrombus is enhanced compared to images obtained after injection of a iomeprol solution.

Example 23

In Vitro Binding using Anti-PEG Construct which Bind Specifically to the Backbone of PEG Chain a. Preparation of Bi-Specific Streptavidin Construct (Anti Mouse P-Selectin Antibody and Anti PEG Antibody E11)
Example 4 is repeated by replacing biotinylated anti mPEG antibody with a biotinylated anti-PEG antibody E11 (see Ref. 30).
b. Preparation of Gas Microbubbles Coated with a Copolymer PEG-Polylysine
DPPS (10 mg) is admixed with 5% propylene glycol-glycerol in water (2 mL). The dispersion is heated to 65° C. for 5 minutes then cooled to room temperature. 1.5 mL of the dispersion are transferred into a vial 2 mL and flushed with $C_4F_{10}$ and shaken for 60 seconds. Resulting microbubbles are washed in water and then incubated with a solution containing 5 mg/mL of PEG-polylysine (Methoxy-poly(ethylene glycol)-block-poly(L-lysine) hydrochloride (Alamanda Polymers, Inc.). Surface coating of microbubbles by PEG-polylysine can be confirmed by Zeta potential measurements.
c. In Vitro Binding on P-Selectin Coated Coverslip in Flow Chamber
Example 7 is repeated except that the microbubbles and bi-specific streptavidin antibodies (anti mouse P-selectin and anti-mPEG B47) are respectively replaced by PEG-polylysine coated microbubbles and bi-specific streptavidin antibodies (anti mouse P-selectin and anti-PEG E11), as prepared above in steps a and b. Good binding of PEG-polylysine coated microbubbles on P-selectin coated surface is obtained.

Example 24

Ultrasound Mediated Gene Delivery Using Anti-PEG Targeting Construct and PEG Containing Microbubbles a. Preparation of Bi-Specific Targeting Construct
Example 4 is repeated by replacing biotinylated IgG anti-P-selectin with a biotin-peptide sequence selected by phage display screening (IPLVVPLGGSC-biotin) which binds specifically to the hepsin receptor over-expressed on LNCaP cells (see Ref. 56).
b. In Vitro Gene Delivery Experiment
The protocol for gene delivery described in Ref. 49 is used. Briefly, LNCaP prostate tumor cells are incubated at 37° C. under 5% $CO_2$ atmosphere, in 225 $cm^2$ tissue culture flasks, in the Mac Coy's 5A medium containing Glutamax-I (Life Technologie, Switzerland), supplemented with 10% v/v heat-inactivated foetal calf serum (FCS) and 1% v/v antibiotics. Gene delivery assays are performed with a plasmid (GFP) with a concentration of 10 µg/mL and a microbubbles/mL cell ratio of 30. The tube is mounted on a rotating exposure system and immersed in a water bath of 37° C. The distance between the transducer and the tube is 7.6 cm. The tubes are insonated for 10 seconds, using a transducer of 2.25 MHz (air-back).
The cells are first incubated with the targeting construct (10 µg/mL) prepared according to step (a) above. After 1 hour, the cells are washed with the medium, re-incubated with mPEG containing microbubbles (see Example 6) and exposed to ultrasound insonation. The cells are then analysed by using a FACS Calibur (Becton Dickinson AG, Switzerland) to determine the percentage of GFP-positive cells and the mean fluorescence intensity of positively transfected cells. Good transfection rate and fluorescent intensity are observed.

Example 25

Ultrasound Imaging Combining Anti-mPEG Targeting Construct and mPEG Containing Microbubbles a. Preparation of Anti-PEG Targeting Construct
Example 4 is repeated by replacing biotinylated IgG anti-P-selectin with a biotin-peptide sequence which binds specifically to the receptor of KDR over-expressed on endothelial cells of angiogenetic vessels of tumors (see e.g. Ref. 39).
b. In Vivo Ultrasound Imaging Studies
$1 \times 10^6$ MATBIII tumor cells are injected into the mammary fat pad of anesthetized female Fisher 344 rats. The rats are divided into two groups to test contrast enhanced imaging (i) mPEG containing gas microvesicles only and (ii) the targeting construct plus mPEG containing gas microvesicles. Contrast enhanced ultrasound imaging is performed at the days 5-7 after tumor induction (tumor size: 0.5~1 cm) using an ultrasound scanner equipped with a probe operating at 7 MHz and CPS contrast imaging mode.
For the rat group (i), 0.4 mL of mPEG containing gas vesicles (Example 6) is injected into the rats and ultrasound is performed 10 minutes after the injection of mPEG containing gas vesicles.
For the rat group (ii), bispecific targeting construct (containing anti-mPEG B-47 and biotinylated peptide KDR) is first injected into the tail of the rats bearing MATBIII tumor. 6 h after the injection of the targeting construct, 0.4 mL of mPEG containing gas vesicles (Example 6) are injected into the rats and ultrasound imaging is performed 10 minutes after the injection of mPEG containing gas vesicles.
Results show that observed contrast effect (LPO: late phase opacification expressed in video intensity) is much stronger in the rats of group (ii).

Example 26

Assessment of Cancer Response to Treatment Using Anti-PEG Targeting Construct and Dual Diagnostic Imaging (Optical and Ultrasound)

a. Preparation of Bi-Specific Targeting Construct (Anti PEG 8-47 and Peptide HVGGSSV)
Anti-PEG targeting construct is prepared with Cy7-labeled streptavidin, biotinylated anti-mPEG B-47 (example 2), and biotinylated peptide sequence HVGGSSV (1:1:2). This peptide is selected by phage display (T7 phage-based random peptide library) and shows specific binding to a tumor which is treated by radiotherapy (see Ref. 57).
b. In Vivo Imaging to Differentiate Responding and Nonresponding Tumors
$1 \times 10^6$ BxpC3 (human pancreatic cancer cells, ATCC) are inoculated into both right and left hind limbs of nude mice and treated when the tumor size reaches 0.5 cm in diameter. Treatment consists of using a tyrosine kinase inhibitor (Sorafenib®, 30 mg/kg) and an irradiation γ (3Gy only at one limb of the mice).
Two imaging techniques (contrast optical and ultrasound) are used for assessment of tumor response to radiotherapy. For optical imaging, NIR (Near-Infrared Fluorescence) images are obtained by using IVIS imaging system (Xenogen). For ultrasound contrast imaging, Siemens Sequoia ultrasound scanner (15L8 probe in CPS mode) and pegylated gas microvesicles are used (Example 6).

The targeting construct (biotinylated anti-mPEG and biotinylated peptide sequence HVGGSSV and Cy7-strepavidin) is injected into mice 2 hours before injection of pegylated gas microvesicles. The optical imaging and contrast ultrasound imaging are performed (24 hours after therapeutic treatment).

Results show that after 1 day treatment (24 hours), the contrast images are enhanced for the irradiated limb both on NIR and ultrasound images, while the limb untreated by irradiation shows negligible contrast effects. These results suggest that anti-PEG targeting construct can be used for the follow-up of cancer therapy.

Optical imaging can be also performed using anti-PEG targeting construct and quantum dots coated with PEG polymers.

Example 27

Tumour Targeting with Liposomal Doxorubicin (Doxil®)

a. Preparation of Bi-Specific Antibodies (Anti Mouse VEGFR2 and Anti mPEG)

Example 13 is repeated by replacing IgG anti-P-selectin with anti-VEGFR2 (CD101, see Ref. 56).

b. In Vivo Administration

U-87 MG tumor cells are injected into the right cerebral hemisphere of a nude mice to establish the intracranial tumors. When tumours grows few millimeters in size, the bispecific antibodies (anti mouse anti VEGFR2 and anti mPEG) are injected to the mice at doses of 20 µg/mice. Doxil®, a commercial preparation of long-circulating mPEG containing liposomes loaded with doxorubicin (Alza Corporation) is administrated to the mice at doses of 3 mg/kg, 6 hours after antibody administration. Prolonged survival of the tumor-bearing mice treated with bispecific antibodies and Doxil® is expected, as compared to survival of mice treated by Doxil® alone at the same dose.

Example 28

Ultrasound Mediated Gene Delivery using Anti-PEG Targeting Construct and PEG Containing Microbubbles a. Preparation of Bi-Specific Targeting Construct Example 4 is repeated by replacing biotinylated IgG anti-P-selectin with a biotin-peptide sequence selected by phage display screening (IPLVVPLGGSC-biotin) which binds specifically to the hepsin receptor over-expressed on LNCaP cells (see Ref. 57).

b. In Vitro Gene Delivery Experiment

The protocol for gene delivery described in Ref. 49 is used. Briefly, LNCaP prostate tumor cells are incubated at 37° C. under 5% $CO_2$ atmosphere, in 225 $cm^2$ tissue culture flasks, in the Mac Coy's 5A medium containing Glutamax-I (Life Technologie, Switzerland), supplemented with 10% v/v heat-inactivated foetal calf serum (FCS) and 1% v/v antibiotics. Gene delivery assays are performed with a plasmid (GFP) with a concentration of 10 µg/mL and a microbubbles/mL cell ratio of 30. The tube is mounted on a rotating exposure system and immersed in a water bath of 37° C. The distance between the transducer and the tube is 7.6 cm. The tubes are insonated for 10 seconds, using a transducer of 2.25 MHz (air-back).

The cells are first incubated with the targeting construct (10 µg/mL) prepared according to step (a) above. After 1 hour, the cells are washed with the medium, re-incubated with mPEG containing microbubbles (see Example 6) and exposed to ultrasound insonation. The cells are then analysed by using a FACS Calibur (Becton Dickinson AG, Switzerland) to determine the percentage of GFP-positive cells and the mean fluorescence intensity of positively transfected cells. Good transfection rate and fluorescent intensity are observed.

Example 29

Ultrasound Imaging Combining Anti-mPEG Targeting Construct and mPEG Containing Microbubbles a. Preparation of Anti-PEG Targeting Construct Example 4 is repeated by replacing biotinylated IgG anti-P-selectin with a biotin-peptide sequence which binds specifically to the receptor of KDR over-expressed on endothelial cells of angiogenetic vessels of tumors (see e.g. Ref. 39).

b. In Vivo Ultrasound Imaging Studies $1 \times 10^6$ MATBIII tumor cells are injected into the mammary fat pad of anesthetized female Fisher 344 rats. The rats are divided into two groups to test contrast enhanced imaging (i) mPEG containing gas microvesicles only and (ii) the targeting construct plus mPEG containing gas microvesicles. Contrast enhanced ultrasound imaging is performed at the days 5-7 after tumor induction (tumor size: 0.5-1 cm) using an ultrasound scanner equipped with a probe operating at 7 MHz and CPS contrast imaging mode.

For the rat group (i), 0.4 mL of mPEG containing gas vesicles (Example 6) is injected into the rats and ultrasound is performed 10 minutes after the injection of mPEG containing gas vesicles.

For the rat group (ii), bispecific targeting construct (containing anti-mPEG B-47 and biotinylated peptide KDR) is first injected into the tail of the rats bearing MATBIII tumor. 6 h after the injection of the targeting construct, 0.4 mL of mPEG containing gas vesicles (Example 6) are injected into the rats and ultrasound imaging is performed 10 minutes after the injection of mPEG containing gas vesicles.

Results show that observed contrast effect (LPO: late phase opacification expressed in video intensity) is much stronger in the rats of group (ii).

Example 30

Assessment of Cancer Response to Treatment using Anti-PEG Targeting Construct and Dual Diagnostic Imaging (Optical and Ultrasound)

a. Preparation of Bi-Specific Targeting Construct (Anti PEG 8-47 and Peptide HVGGSSV)

Anti-PEG targeting construct is prepared with Cy7-labeled streptavidin, biotinylated anti-mPEG B-47 (example 2), and biotinylated peptide sequence HVGGSSV (1:1:2). This peptide is selected by phage display (T7 phage-based random peptide library) and shows specific binding to a tumor which is treated by radiotherapy (see Ref. 58).

b. In Vivo Imaging to Differentiate Responding and Nonresponding Tumors $1 \times 10^6$ BxpC3 (human pancreatic cancer cells, ATCC) are inoculated into both right and left hind limbs of nude mice and treated when the tumor size reaches 0.5 cm in diameter. Treatment consists of using a tyrosine kinase inhibitor (Sorafenib®, 30 mg/kg) and an irradiation γ (3Gy only at one limb of the mice).

Two imaging techniques (contrast optical and ultrasound) are used for assessment of tumor response to radiotherapy. For optical imaging, NIR (Near-Infrared Fluorescence) images are obtained by using IVIS imaging system (Xenogen). For ultrasound contrast imaging, Siemens Sequoia ultrasound scanner (15L8 probe in CPS mode) and pegylated gas microvesicles are used (Example 6).

The targeting construct (biotinylated anti-mPEG and biotinylated peptide sequence HVGGSSV and Cy7-strepavidin) is injected into mice 2 hours before injection of pegylated gas microvesicles. The optical imaging and contrast ultrasound imaging are performed (24 hours after therapeutic treatment).

Results show that after 1 day treatment (24 hours), the contrast images are enhanced for the irradiated limb both on NIR and ultrasound images, while the limb untreated by irradiation shows negligible contrast effects. These results suggest that anti-PEG targeting construct can be used for the follow-up of cancer therapy.

Optical imaging can be also performed using anti-PEG targeting construct and quantum dots coated with PEG polymers.

LIST OF CITED REFERENCES

1. U.S. Pat. No. 6,217,849 (BRACCO RESEARCH S.A.)
2. U.S. Pat. No. 5,387,410 (Mallinckrodt Inc.)
3. U.S. Pat. No. 5,271,928 (BRACCO INTERNATIONAL B.V.)
4. U.S. Pat. No. 5,413,774 (BRACCO INTERNATIONAL B.V.)
5. U.S. Pat. No. 5,827,504 (BRACCO RESEARCH S.A.)
6. U.S. Pat. No. 5,597,549 (BRACCO INTERNATIONAL B.V.)
7. Int. Pat. Appl. Pub. No. WO 04/069284 (BRACCO INTERNATIONAL B.V.)
8. U.S. Pat. No. 5,711,933 (BRACCO INTERNATIONAL B.V.)
9. U.S. Pat. No. 6,333,021 (BRACCO RESEARCH S.A.)
10. Cassidy, P. J.; Radda, G. K. "*Molecular imaging perspectives*", J.R. Soc. Interface, 2005, 2(3), 133-144.
11. Sharma, V.; Luker, G. D.; Piwnica-Worms, D. "*Molecular imaging of gene expression and protein function in vivo with PET and SPECT*", J. Magn Reson. Imaging, 2002, 16(4), 336-351.
12. Goins, B. A.; Phillips, W. T. "*The use of scintigraphic imaging as a tool in the development of liposome formulations*", Prog. Lipid Res., 2001, 40(1-2), 95-123.
13. Torchilin, V. P. "*Targeted pharmaceutical nanocarriers for cancer therapy and imaging*", AAPS. J., 2007, 9(2), E128-E147.
14. Making and using antibodies: A practical handbook, CRC press: 2007; Chapter 4, 5 and 9.
15. Kohler, G.; Milstein, C. "*Continuous cultures of fused cells secreting antibody of predefined specificity*", Nature, 1975, 256(5517), 495-7.
16. U.S. Pat. No. 4,816,567 (Genentech Inc.)
17. Babcook, J. S.; Leslie, K. B.; Olsen, 0. A.; Salmon, R. A.; Schrader, J. W. "*A novel strategy for generating monoclonal antibodies from single, isolated lymphocytes producing antibodies of defined specificities*", Proc Natl Acad Sci USA, 1996, 93(15), 7843-8.
18. Pasqualini, R.; Arap, W. "*Hybridoma-free generation of monoclonal antibodies*", Proc Natl Acad Sci USA, 2004, 101(1), 257-9.
19. U.S. Pat. No. 5,969,108 (Medical Research Council)
20. Okamoto, T.; Mukai, Y.; Yoshioka, Y.; Shibata, H.; Kawamura, M.; Yamamoto, Y.; Nakagawa, S.; Kamada, H.; Hayakawa, T.; Mayumi, T.; Tsutsumi, Y. "*Optimal construction of non-immune scFv phage display libraries from mouse bone marrow and spleen established to select specific scFvs efficiently binding to antigen*", Biochem Biophys Res Commun, 2004, 323(2), 583-91.
21. Wu, B. P.; Xiao, B.; Wan, T. M.; Zhang, Y. L.; Zhang, Z. S.; Zhou, D. Y.; Lai, Z. S.; Gao, C. F. "*Construction and selection of the natural immune Fab antibody phage display library from patients with colorectal cancer*", World J Gastroenterol, 2001, 7(6), 811-5.
22. Yau, K. Y.; Dubuc, G.; Li, S.; Hirama, T.; Mackenzie, C. R.; Jermutus, L.; Hall, J. C.; Tanha, J. "*Affinity maturation of a V(H)H by mutational hotspot randomization*", J Immunol Methods, 2005, 297(1-2), 213-24.
23. U.S. Pat. No. 5,837,821 (City of Hope)
24. Quiocho, F. A. "*Protein engineering. Making of the minibody*", Nature, 1993, 362(6418), 293-4.
25. Pat. Appl. Publ. No. EP 404 097 (Genentech Inc.)
26. Holliger, P.; Prospero, T.; Winter, G. ""*Diabodies*": *small bivalent and bispecific antibody fragments*", Proc Natl Acad Sci USA, 1993, 90(14), 6444-8.
27. Holliger, P.; Hudson, P. J. "*Engineered antibody fragments and the rise of single domains*", 2005, 23(9), 1126-1136.
28. Bird, R. E.; Hardman, K. D.; Jacobson, J. W.; Johnson, S.; Kaufman, B. M.; Lee, S. M.; Lee, T.; Pope, S. H.; Riordan, G. S.; Whitlow, M. "*Single-chain antigen-binding proteins*", Science, 1988, 242(4877), 423-6.
29. U.S. Pat. No. 4,946,778 (Genex Corp)
30. Cheng, T. L.; Cheng, C. M.; Chen, B. M.; Tsao, D. A.; Chuang, K. H.; Hsiao, S. W.; Lin, Y. H.; Roffler, S. R. "*Monoclonal antibody-based quantitation of poly(ethylene glycol)-derivatized proteins, liposomes, and nanoparticles*", Bioconjug.Chem., 2005, 16(5), 1225-1231.
31. Pat. Appl. Publ. No. US 2001/028881 (Academia Sinica)
32. Int. Pat. Appl. Pub. No. WO 02/094853 (Shearwater Corp.)
33. Int. Pat. Appl. Pub. No. WO 98/18501 (Nycomed Imaging AS)
34. Int. Pat. Appl. Publ. No WO 2008/073458 (BRACCO IMAGING SpA)
35. Int. Pat. Appl. Publ. No. WO 01/09188 (EPIX Medical Inc.)
36. Int. Pat. Appl. Publ. No. WO 02/55544 (DYAX CORP.)
37. Int. Pat. Appl. Pub. No. WO 03/74005 (DYAX CORP. and BRACCO INTERNATIONAL B.V.)
38. Int. Pat. Appl. Publ. No. WO 03/84574 (BRACCO INTERNATIONAL B.V. and DYAX CORP.)
39. Int. Pat. Appl. Pub. No. WO 2006/031885 (DYAX CORP. and BRACCO INTERNATIONAL B.V.)
40. Int. Pat. Appl. Pub. No. WO 2007/109475 (BRACCO IMAGING SpA)
41. von Wronski, M. A.; Raju, N.; Pillai, R.; Bogdan, N. J.; Marinelli, E. R.; Nanjappan, P.; Ramalingam, K.; Arunachalam, T.; Eaton, S.; Linder, K. E.; Yan, F.; Pochon, S.; Tweedle, M. F.; Nunn, A. D. "*Tuftsin binds neuropilin-1 through a sequence similar to that encoded by exon 8 of vascular endothelial growth factor*", J. Biol. Chem., 2006, 281(9), 5702-5710.
42. Int. Pat. Appl. Pub. No. WO 97/29782 (Nycomed Imaging AS)
43. U.S. Pat. No. 5,605,673 (Alliance Pharmaceutical Corp.)
44. U.S. Pat. No. 4,276,885 (Rasor Associates Inc.)
45. Pat. Appl. Publ. No. EP 324 938 (Molecular Biosystems Inc.)
46. Int. Pat. Appl. Publ. No. WO 94/09829 (BRACCO INTERNATIONAL B.V.)

47. Int. Pat. Appl. Publ. No. WO 99/39738 (BRACCO RESEARCH S.A.)
48. Int. Pat. Appl. Publ. No. WO 2005/063305 (BRACCO RESEARCH S.A.)
49. Int. Pat. Appl. Publ. No. WO 2006/111490 (BRACCO RESEARCH S.A.)
50. Int. Pat. Appl. No. WO 92/10166 (SINTETICA S.A.)
51. M. Malmsten in *Surfactants and Polymers in Drug Delivery*, Marcel Dekker Inc., editor; 2002; Chapter 4, pp. 87-113.
52. Int. Pat. Appl. Pub. No. WO 05/117832 (BRACCO RESEARCH, S. A.)
53. U.S. Pat. No. 5,545,395 (BRACCO RESEARCH S.A.)
54. Golman, K.; Ardenkjaer-Larsen, J. H.; Petersson, J. S.; Mansson, S.; Leunbach, I. "*Molecular imaging with endogenous substances*", Proc. Natl. Acad. Sci. U.S.A, 2003, 100(18), 10435-10439.
55. Johansson, E.; Olsson, L. E.; Mansson, S.; Petersson, J. S.; Golman, K.; Stahlberg, F.; Wirestam, R. "*Perfusion assessment with bolus differentiation: a technique applicable to hyperpolarized tracers*", Magn Reson. Med., 2004, 52(5), 1043-1051.
56. Sweeney, P.; Karashima, T.; Kim, S. J.; Kedar, D.; Mian, B.; Huang, S.; Baker, C.; Fan, Z.; Hicklin, D. J.; Pettaway, C. A.; Dinney, C. P. "*Anti-vascular endothelial growth factor receptor 2 antibody reduces tumorigenicity and metastasis in orthotopic prostate cancer xenografts via induction of endothelial cell apoptosis and reduction of endothelial cell matrix metalloproteinase type 9 production*", Clin. Cancer Res., 2002, 8(8), 2714-2724.
57. Kelly, K. A.; Setlur, S. R.; Ross, R.; Anbazhagan, R.; Waterman, P.; Rubin, M. A.; Weissleder, R. "*Detection of early prostate cancer using a hepsin-targeted imaging agent*", Cancer Res., 2008, 68(7), 2286-2291.
58. Han, Z.; Fu, A.; Wang, H.; Diaz, R.; Geng, L.; Onishko, H.; Hallahan, D. E. "*Noninvasive assessment of cancer response to therapy*", Nat. Med., 2008, 14(3), 343-349.

The invention claimed is:

1. A pharmaceutical kit comprising:
    a) a first composition comprising a liposome or a gas-filled microvesicle, or a precursor thereof, having a stabilizing envelope comprising a plurality of polymer molecules said polymer being polyethylene glycol comprising repeating oxyethylene units; and
    b) a second composition comprising a targeting construct, said construct comprising a targeting ligand and an antibody capable of selectively binding to a sequence of said repeating oxyethylene units of said polymer,
        wherein said targeting ligand is associated non-covalently with said antibody to form said targeting construct, and wherein said targeting construct is in the form of a micelle or of a liposome.

2. A pharmaceutical kit according to claim 1, wherein said polymer is a hydrophilic polymer.

3. A pharmaceutical kit according to claim 1, wherein said polymer is terminated with a methoxy group.

4. A pharmaceutical kit according to claim 3, wherein said antibody selectively binds to a sequence of repeating oxyethylene units terminated with a methoxy group.

5. A pharmaceutical kit according to claim 1, wherein said polymer is present in a molar amount of at least 0.05% with respect to the total amount of components of said stabilizing envelope.

6. A pharmaceutical kit according to claim 5, wherein said molar amount is of at least 0.2%.

7. A pharmaceutical kit according to claim 5, wherein said molar amount is of at least 1%.

8. A pharmaceutical kit according to claim 1, wherein said gas-filled microvesicle comprises more than 50% by mole of phospholipids.

9. A pharmaceutical kit according to claim 1, wherein said liposome comprises a therapeutic agent or a contrast agent.

10. A liposome or gas-filled microvesicle, or a precursor thereof, comprising: a) a polyethylene glycol comprising repeating oxyethylene units; b) an antibody bound to said repeating oxyethylene units; and c) a targeting ligand associated with said antibody, wherein said targeting ligand is associated non-covalently with said antibody to form a targeting construct, and wherein said targeting construct is in the form of a micelle or of a liposome.

* * * * *